(12) United States Patent
Asari et al.

(10) Patent No.: US 10,206,985 B2
(45) Date of Patent: Feb. 19, 2019

(54) WT1 PEPTIDE CANCER VACCINE COMPOSITION FOR MUCOSAL ADMINISTRATION

(71) Applicants: NITTO DENKO CORPORATION, Osaka (JP); OSAKA UNIVERSITY, Osaka (JP)

(72) Inventors: Daisuke Asari, Osaka (JP); Kyohei Matsushita, Osaka (JP); Arimichi Okazaki, Osaka (JP); Yoshiki Maeda, Osaka (JP); Katsuyuki Okubo, Osaka (JP); Mitsuhiko Hori, Osaka (JP); Haruo Sugiyama, Osaka (JP)

(73) Assignees: NITTO DENKO CORPORATION, Osaka (JP); OSAKA UNIVERSITY, Osaka (JP)

(*) Notice: Subject to any disclaimer, the term of this patent is extended or adjusted under 35 U.S.C. 154(b) by 0 days.

(21) Appl. No.: 14/166,970

(22) Filed: Jan. 29, 2014

(65) Prior Publication Data

US 2014/0220059 A1    Aug. 7, 2014

(30) Foreign Application Priority Data

Feb. 5, 2013   (JP) .................. 2013-020904

(51) Int. Cl.
*A61K 39/00* (2006.01)
*A61K 9/00* (2006.01)

(52) U.S. Cl.
CPC .......... *A61K 39/0011* (2013.01); *A61K 9/006* (2013.01); *A61K 9/0043* (2013.01); *A61K 2039/541* (2013.01); *A61K 2039/542* (2013.01)

(58) Field of Classification Search
None
See application file for complete search history.

(56) References Cited

U.S. PATENT DOCUMENTS

| | | | |
|---|---|---|---|
| 7,030,212 B1 | 4/2006 | Sugiyama et al. | |
| 9,056,069 B2* | 6/2015 | Singh | A61K 38/2013 |
| 2003/0082194 A1* | 5/2003 | Gaiger | C07K 14/4748 424/184.1 |
| 2003/0232055 A1* | 12/2003 | Medzhitov | A61K 39/385 424/185.1 |
| 2005/0215501 A1* | 9/2005 | Lipford et al. | 514/44 |
| 2008/0112974 A1 | 5/2008 | Czerkinsky et al. | |
| 2008/0193487 A1 | 8/2008 | Schild et al. | |
| 2008/0286296 A1 | 11/2008 | Ebensen et al. | |
| 2010/0221223 A1 | 9/2010 | Tsutsui et al. | |
| 2011/0070251 A1* | 3/2011 | Sugiyama | 424/185.1 |
| 2011/0293723 A1* | 12/2011 | Bratzler | A61K 9/5153 424/489 |
| 2012/0045465 A1* | 2/2012 | Sugiyama | 424/185.1 |
| 2012/0052080 A1* | 3/2012 | Okada | A61K 9/0019 424/184.1 |
| 2015/0150975 A1* | 6/2015 | Tanaka | A61K 47/12 424/185.1 |

FOREIGN PATENT DOCUMENTS

| | | |
|---|---|---|
| CN | 1549726 | 11/2004 |
| CN | 101888852 | 11/2010 |
| CN | 102803487 | 11/2012 |
| EP | 2 228 072 A1 | 9/2010 |
| JP | 7-505883 A | 6/1995 |
| JP | 2002-531415 A | 9/2002 |
| JP | 2005-518192 A | 6/2005 |
| JP | 2007-515393 A | 6/2007 |
| JP | 2007-529531 A | 10/2007 |
| JP | 2008127277 A * | 6/2008 |
| JP | 2009-511637 A | 3/2009 |
| JP | 4422903 B2 | 12/2009 |
| RU | 2192884 A | 11/2002 |
| WO | 93/20847 A1 | 10/1993 |
| WO | 00/32228 A2 | 6/2000 |
| WO | 01/25273 A2 | 4/2001 |
| WO | 01/62920 A2 | 8/2001 |
| WO | 02/09748 | 2/2002 |
| WO | 03/037060 A | 5/2003 |
| WO | 2004/028561 A | 4/2004 |
| WO | 2004/100870 A | 11/2004 |
| WO | 2005/087238 A2 | 9/2005 |
| WO | 2007/047764 A | 4/2007 |
| WO | 2009/072610 A | 6/2009 |
| WO | 2011/026111 A1 | 3/2011 |
| WO | 2011/151431 A | 12/2011 |

OTHER PUBLICATIONS

Hearnden et al (Advanced Drug Delivery Reviews, Jan. 2012, 64:16-28).*
Lim, Int. Immunopharmacol. Jan. 2003;3(1):115-118.*
Taniguchi et al. Anticancer Res. 2006; 26: 3997-4002.*
Yoshida et al., Anticancer Res. Nov. 2009;29(11):4867-487.*
Kohchi et al., J Biosci Bioeng. Dec. 2006;102(6):485-496.*
Kikuchi et al., Immunology. Jan. 2006;117(1):47-58.*
Russo et al., Blood. May 26, 2011;117(21):5683-91 (Year: 2011).*
Zhengrong Cui et al., Pharmaceutical Research, vol. 19, No. 7, 2002, pp. 947-953.
Hosoi Akihiro et al., Cancer Research, 68, 2008, pp. 3941-3949.
Yoshihiro Oka et al., Current Opinion in Immunology, 2008, 20: 211-220.
European Search Report in regards to European Application No. 14000325.2, dated Apr. 7, 2014.
European Office Action issued with respect to European application No. 14000325.2, dated Dec. 16, 2016.

(Continued)

*Primary Examiner* — Daniel C Gamett

(74) *Attorney, Agent, or Firm* — Greenblum & Bernstein, P.L.C.

(57) ABSTRACT

The present invention provides a cancer vaccine composition for mucosal administration for inducing cellular immunity, comprising (i) a WT1 peptide and/or a modified WT1 peptide; and (ii) a cellular immunity induction promoter. The composition efficiently induces cellular immunity against a cancer in a subject.

22 Claims, No Drawings

Specification includes a Sequence Listing.

(56) References Cited

OTHER PUBLICATIONS

Chinese Office Action issued in Counterpart Patent Appl. No. 20140043724.4, dated May 19, 2017, along with an english translation thereof.
Japanese Office Action with English Translation in respect to Japanese Application No. 2014-014812, dated Nov. 7, 2017.
Russian Office Action and Search Report with English Translation in respect to Russian Application No. 2014102946, dated Dec. 26, 2017.
European Office Action in respect to European Application No. 14000325.2, dated Jan. 8, 2018.
Fujiki, Fumihiro et al., "A WT1 protein-derived, naturally processed 16-mer peptide, WT1332, is a promiscuous helper peptide for induction of WT1-specific Th1-type CD4+ T cells," Microbiol. Immunol., 2008, vol. 52, pp. 591-600.
Oka, Yoshihiro, et al., "WT1 Peptide Vaccination Therapy Targeting Hematological Malignancies and Solid Cancers," Biotherapy, 2009, vol. 23, No. 2, pp. 170-177 with English Summary.
Oka, Yoshihiro, et al., "Cancer antigen WT1-targeting treatment for the malignancies—Development of WT1 peptide vaccine," Jpn J Clin Immunol., 2008, vol. 31, No. 5, pp. 375-382 with English Summary.
Abstract from "Treatment of Malignant Brain Tumor with WT1 Peptide," from the Journal of Japan Society for Cancer Therapy, 2010, vol. 45, No. 2, pp. 384 (S30-7) with English Translation.
Abstract from "Utilization of Mucous Membrane for the Purpose of Enhancement of Efficacy of Cancer Vaccination Therapy," from the Japan Society of Immunology & Allergology in Otolaryngology, Program, 2009, vol. 27, pp. 53 with English Translation.
Allam, Jean-Pierre, et al., "Toll-like receptor 4 ligation enforcers tolerogenic properties of oral mucosal Langerhans cells." J. Allergy Clin. Immunol., 2008, vol. 121, pp. 368-374.
Aoyama-Kondo, Tatsuko, et al. "Characterization of Antibody Responses of Local Lymph Nodes to Antigen Given under the Oral Submucosa," Immunobiol., 1992, vol. 184, pp. 372-383.
Karande et al., "Transcutaneous Immunization: An Overview of Advantages, Disease targets, Vaccines, and Delivery Technologies," Annual Review of Chemical and Biomolecular Engineering, 2010, vol. 1, pp. 175-201.

\* cited by examiner

WT1 PEPTIDE CANCER VACCINE COMPOSITION FOR MUCOSAL ADMINISTRATION

SEQUENCE LISTING

The instant application contains a Sequence Listing which has been submitted electronically in ASCII format and is hereby incorporated by reference in its entirety. Said ASCII copy, created on Mar. 24, 2014, is named P45221_SL.txt and is 2,603 bytes in size.

TECHNICAL FIELD

The present invention relates to a cancer vaccine for mucosal administration comprising a WT1 peptide and/or a modified WT1 peptide, and a cellular immunity induction promoter.

BACKGROUND ART

There are a cancer vaccine that prevents virus infection to prevent a cancer caused by a virus, and a cancer vaccine which provides the result that cancer cells are specifically attacked by the immune system via the recognition of a cancer-specific antigen by the immune mechanism, particularly, the cellular immune mechanism in which cytotoxic T cell (CTL) plays an important role. The former is not effective at all for a cancer in which the virus dose not participate. The latter is a cancer therapeutic strategy of targeting an antigen possessed by a cancer cell itself. It is considered that the latter is widely effective for cancers having antigen by specifying the antigen. Inter alia, a cancer vaccine based on the viewpoint of the latter can treat tumors that are difficult to remove by surgical operation because of their size, and causes less side effects as compared with the previous therapies such as chemotherapy and radiation therapy.

WT1 (Wilm's tumor 1) gene is overexpressed in many hematopoietic tumors and solid cancers, for example, acute myelocytic leukemia, acute lymphocytic leukemia, chronic myelocytic leukemia, myelodysplastic syndrome, multiple myeloma, non-Hodgkin's lymphoma, lung cancer, breast cancer, stomach cancer, large intestine/rectum cancer, pancreas cancer, bile duct cancer, head and neck squamous cell cancer, thyroid cancer, kidney cancer, prostate cancer, ovarian cancer, uterine cancer, bone soft tissue sarcoma, malignant melanoma, malignant mesothelioma, testicular germ cell tumor and malignant glioma. Those cancers overproduce the WT1 protein. The WT1 protein is fragmented in a cancer cell to produce partial peptides consisting of 8 to 12 amino acids. A WT1 peptide is one of the peptide fragment which has been bound with the MHC class I molecule in a cancer cell, moved to the surface of the cancer cell, and presented as an antigen bound to the MHC class I molecule on the cancer cell surface. The WT1 peptide becomes a mark of the cancer cell. The amino acid sequence of the WT1 peptide conforms to the type of the MHC class I molecule of the cell. For example, in the case of a cell having HLA-A*0201-type MHC, a HLA-A*0201-type MHC restricted WT1 peptide such as Db126 peptide consisting of 9 amino acids is generated, and in the case of a cell having HLA-A*2402-type MHC, a HLA-A*2402-type MHC restricted WT1 peptide such as Db235 peptide consisting of 9 amino acids is generated. In the case of a cell having other MHC, such as HLA-A26 type (WO2005/095598), HLA-A*3303 type (WO 2007/097358), or HLA-A*1101 type (WO 2008/081701), each MHC restricted WT1 peptide is generated. When a WT1 peptide, or a modified WT1 peptide in which a part of amino acids of the WT1 peptide is substituted or modified is administered to a living body as an antigen (herein, a WT1 peptide or a modified WT1 peptide which has been administered as an antigen is referred to as "WT1 antigen peptide"), the WT1 antigen peptide is bound to the MHC Class I molecule on the surface of a dendritic cell which is an antigen presenting cell, or the WT1 antigen peptide is once taken into a dendritic cell, bound to the MHC class I molecule od the dendritic cell and then, is moved to the surface of the dendritic cell, thereby, is presented as an antigen bound to the MHC class I molecule on the surface of the dendritic cell. An activated dendritic cell having the WT1 antigen peptide/MHC class I molecule complex is moved to the regional lymph node, and activates a CD8-positive T lymphocyte which recognizes the WT1 antigen peptide/MHC class I molecule complex to differentiate and proliferate the cell into a cytotoxic T cell (CTL). CTL recognizes tumor cells having the complex of a WT1 peptide (derived from an endogenous WT1 protein) of the same amino acid sequence as the WT1 antigen peptide and the MHC class I molecule, or a tumor cell having a complex of a WT1 peptide (derived from an endogenous WT1 protein) of an amino acid sequence having cross immunoreactivity with the WT1 antigen peptide and the MHC class I molecule, and attacks the recognized tumor cells. Therefore, the aforementioned various MHC restricted WT1 peptides such as Db126 peptide and Db235 peptide, and modified WT1 peptides in which a part of amino acids of them are substituted or modified are useful as cancer vaccines (Non-Patent Document 1).

It is also known that an adjuvant is utilized in order to enhance the action as cancer vaccine of the WT1 peptide and/or the modified WT1 peptide. As the adjuvant for the WT1 peptide and/or the modified WT1 peptide, for example, mineral gels such as aluminum hydroxide; surfactants such as lysolecithin, and pluronicpolyol; polyanions; peptides; or oil emulsions (Patent Document 1), and GM-CSF, BCG-CWS and Montanide ISA51 (Non-Patent Document 1) are known. In addition to them, a variety of vaccine adjuvants including cyclic dinucleotide analogs (Patent Document 3 and Patent Document 4) such as 1H-imidazo[4,5-c]quinoline-4-amine, imiquimod (Patent Document 2), and cyclic di-GMP (c-di-GMP), and TLR2, 3, 7, 8 and 9 ligands (Patent Document 5) have been known. In addition, it is also known that immunity induced by transdermal administration of imiquimod-containing peptide is further enhanced by adding Peptide-25 (Non-Patent Document 2).

In general, vaccines are administered by subcutaneous or intradermal injection. In addition to those routes, immunity induction by a variety of administration routes, for example, transdermal administration (Patent Document 5 and Non-Patent Document 2), and mucosal administration such as, buccal administration, nasal administration, and sublingual administration (Non-Patent Document 3, Patent Document 6, and Patent Document 7) have been tried.

LIST OF DOCUMENTS

[Patent Document 1] Japanese Patent No. 4422903
[Patent Document 2] JP 7-505883 A
[Patent Document 3] JP 2007-529531 A
[Patent Document 4] US Patent Application Publication No. 2008/0286296
[Patent Document 5] US Patent Application Publication No. 2008/0193487

[Patent Document 6] JP 2002-531415 A
[Patent Document 7] US Patent Application Publication No. 2008/0112974
[Non-Patent Document 1] Yoshihiro Oka et al., Current Opinion in Immunology, 20: 211-220 (2008)
[Non-Patent Document 2] Hosoi Akihiro et al., Cancer Research, 68, 3941-3949 (2008)
[Non-Patent Document 3] Zhengrong Cui et al., Pharmaceutical Research, Vol. 19, No. 7, 947-953 (2002)

SUMMARY OF THE INVENTION

It is well-known that an adjuvant is used to enhance efficacy of a vaccine. Suitable adjuvant generally varies depending on, for example, the kind of the antigen, the administration route, and the immune response which is desired to be induced (i.e. cellular immunity or humoral immunity). Further, in addition to the adjuvant, there are a variety of substances which promote the induction of the immunity. Then, an object of the present invention is to provide a composition for use as a cancer vaccine with higher efficacy and is convenient for use.

A microorganism or a virus itself, or a part of them is contained in a widely used vaccine, and the vaccine is administered to induce immune response. Usually, invasion of the microorganism or virus is inhibited by the skin due to the size thereof. Also the microorganism or virus is degraded by gastric acid and digestive enzymes. Thus, it is necessary that the vaccine is invasively administered into the body. From such viewpoint, vaccines have been usually administered into the body by injection. However, the injection has some problems including pain, fear, injection scar, and subsequent scarring cicatrization. People other than health care workers are not permitted to perform the injection. Intradermal injection which can introduce higher immune response is a difficult administration technique. There is a risk of accidental infection of the health care workers due to needlestick injury. Patient are needed to visit the hospital repeatedly when administration is performed repetitively. Medical wastes which necessitate special disposition such as an injection needle are generated. In view of the above issues, injection is not necessarily the optimal administration route.

A WT1 peptide and/or the modified WT1 peptide can activate CTL (cytotoxic T cell) via a MHC class I molecule, that is, the peptide can induce cellular immunity. The WT1 peptide and/or the modified WT1 peptide are a molecule having a molecular weight of about 700 to about 1600 and consisting of 8 to 12 amino acids, and are considerably smaller than microorganisms or virus itself although they are not considered as a small-molecule substance. It may be possible that they are administered by a route other than injection. However, a preparation for the administration of the peptide vaccine in a rout other than injection has not been developed yet. The reason includes many things, for example: a suitable substance that can promote to induce the cellular immunity has been unknown; it has also been unknown whether or not an antigen can be delivered to a tissue suitable for the induction of the cellular immunity. Inter alia, a substance that can promote to induce the cellular immunity when it is used with the antigen when administered in a route other than injection has been unknown.

The inventors have found that the cellular immunity can effectively be induced by mucosal administration of the peptide vaccine. The inventors have also found some substances suitable for enhancing cellular immunity induced by the mucosal administration of a WT1 peptide and/or a modified WT1 peptide. The substances may include TLR ligands such as $Pam_3CSK_4$, Poly(I:C), lipopolysaccharide, imiquimod, and resiquimod; cyclic dinucleotides such as cyclic di-GMP and cyclic di-AMP; immunomodulatory small molecule drugs such as levamisole hydrochloride; cyclooxygenase inhibitors such as etodolac and loxoprofen; prostaglandin receptor antagonists such as an EP2 receptor antagonist, an EP4 receptor antagonist, a DP receptor antagonist, and an IP receptor antagonist; prostaglandin receptor agonists such as an EP3 receptor agonist; TSLP production inhibitors such as berberine chloride and naringenin; adenylate cyclase inhibitors such as 2',5'-dideoxyadenosine and niacin; omega-3 fatty acids such as eicosapentaenoic acid and docosahexaenoic acid; PPAR agonists such as a PPAR-α agonist, a PPAR-δ agonist, and a PPAR-γ agonist; dopamine receptor antagonists such as a D1 receptor antagonist, and a D5 receptor antagonist; dopamine receptor agonists such as a D2 receptor agonist, a D3 receptor agonist, and a D4 receptor agonist; histamine receptor antagonists such as a H1 receptor antagonist, and a H2 receptor antagonist; histamine receptor agonists such as a H1 receptor agonist, a H3 receptor agonist, and a H4 receptor agonist; serotonin receptor antagonists such as a 5-HT2 receptor antagonist, a 5-HT4 receptor antagonist, a 5-HT6 receptor antagonist and a 5-HT7 receptor antagonist; serotonin receptor agonists such as a 5-HT1 receptor agonist, and a 5-HT2 receptor agonist; vasopressin receptor antagonists such as a V2 receptor antagonist; vasopressin receptor agonists such as a V1 receptor agonist; muscarine receptor antagonists such as a M1 receptor antagonist, a M3 receptor antagonist, and a M5 receptor antagonist; muscarine receptor agonists such as a M1 receptor agonist, a M2 receptor agonist, a M3 receptor agonist, a M4 receptor agonist, and a M5 receptor agonist; adrenalin receptor antagonists such as an α1 receptor antagonist, a β1 preceptor antagonist, a β2 receptor antagonist, and a β3 receptor antagonist; adrenalin receptor agonists such as an α1 receptor agonist, and an α2 receptor agonist; angiotensin receptor agonists such as an AT2 receptor agonist; GABA receptor agonists such a $GABA_B$ receptor agonist; thrombin receptor antagonists such as a PAR-1 receptor antagonist; thrombin receptor agonists such as a PAR-1 receptor agonist; opioid receptor agonists such as buprenorphine; leukotriene receptor antagonists such as a CysLT1 receptor antagonist and a CysLT2 receptor antagonist; leukotriene receptor agonists such as a BLT receptor agonist; ADP receptor agonists such as adenosine diphosphate; melatonin receptor agonists such as melatonin; somatostatin receptor agonists such as octreotide; cannabinoid receptor agonists such as dronabinol; sphingosine-1 phosphate receptor agonists such as fingolimod; metabotropic glutamate receptor agonists such as an mGluR2 receptor agonist, an mGluR3 receptor agonist, an mGluR4 receptor agonist, an mGluR6 receptor agonist, an mGluR7 receptor agonist, and an mGluR8 receptor agonist; phospholipase A2 inhibitors such as glycyrrhizic acid; TGF-β production inhibitors such as pirfenidone; Th2 cytokine inhibitors such as suplatast tosylate; pharmacologically acceptable acids such as decanoic acid, lauric acid, myristic acid, isostearic acid, and oleic acid, or pharmacologically acceptable salts thereof; and helper peptides such as Peptide-25.

In oral mucosal administration, inter alia, it is found that TLR1/2 ligand such as $Pam_2CSK_4$; a TLR2/6 ligand such as $Pam_2CSK_4$, MALP-2 and FSL-1; a TLR4 ligand such as lipopolysaccharide, lipid A, and monophosphoryl lipid; a TLR7 and/or TLR8 ligand such as imiquimod, resiquimod, loxoribine, and TLR7-II; a cyclic dinucleotide such as cyclic di-GMP, and cyclic di-AMP; an immunomodulatory small molecule drug such as levamisole hydrochloride; a helper peptide; a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, a Th2 cytokine inhibitor; or a combination of two or more thereof is suitable to promote the induction of the cellular immunity. Further, it was also found that cellular immunity is remarkably enhanced by a combination of a TLR ligand and a helper peptide, a combination of a cyclic dinucleotide and a helper peptide, a combination of an immunomodulatory small molecule drug and a helper peptide, a combination of a cyclooxygenase inhibitor and a helper peptide, a combination of a prostaglandin receptor antagonist and a helper peptide, a combination of a prostaglandin receptor agonist and a helper peptide, a combination of a TSLP production inhibitor and a helper peptide, a combination of an adenylate cyclase inhibitor and a helper peptide, a combination of an omega-3 fatty acid and a helper peptide, a combination of a PPAR agonist and a helper peptide, a combination of a dopamine receptor antagonist and a helper peptide, a combination of a dopamine receptor agonist and a helper peptide, a combination of a histamine receptor agonist and a helper peptide, a combination of a histamine receptor antagonist and a helper peptide, a combination of a serotonin receptor agonist and a helper peptide, a combination of a serotonin receptor antagonist and a helper peptide, a combination of a vasopressin receptor antagonist and a helper peptide, a combination of a vasopressin receptor agonist and a helper peptide, a combination of a muscarine receptor antagonist and a helper peptide, a combination of a muscarine receptor agonist and a helper peptide, a combination of an adrenalin receptor antagonist and a helper peptide, a combination of an adrenalin receptor agonist and a helper peptide, a combination of an angiotensin receptor agonist and a helper peptide, a combination of a GABA receptor agonist and a helper peptide, a combination of a thrombin receptor antagonist and a helper peptide, a combination of a thrombin receptor agonist and a helper peptide, a combination of an opioid receptor agonist and a helper peptide, a combination of an ADP receptor agonist and a helper peptide, a combination of a leukotriene receptor antagonist and a helper peptide, a combination of a leukotriene receptor agonist and a helper peptide, a combination of a melatonin receptor agonist and a helper peptide, a combination of a somatostatin receptor agonist and a helper peptide, a combination of a cannabinoid receptor agonist and a helper peptide, a combination of a sphingosine-1 phosphate receptor agonist and a helper peptide, a combination of a metabotropic glutamate receptor agonist and a helper peptide, a combination of a phospholipase A2 inhibitor and a helper peptide, a combination of a TGF-β production inhibitor and a helper peptide, a combination of a Th2 cytokine inhibitor and a helper peptide, or a combination of a pharmacologically acceptable acid or a pharmacologically acceptable salt thereof and a helper peptide.

Further, it was found that, in a nasal mucosa, inter alia, TLR2 and Dectin1 ligands such as Zymosan; TLR3 ligands such as Poly(I:C); and immunomodulatory small molecule drugs such as pidotimod and bestatin are effective, as well as aforementioned cellular immunity induction promoters for oral mucosal administration.

Therefore, the present invention, in a first aspect, provides the aspects listed below:

(1) A cancer vaccine composition for mucosal administration for inducing cellular immunity, comprising:
(i) a WT1 peptide and/or a modified WT1 peptide; and
(ii) a first cellular immunity induction promoter selected from a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, a Th2 cytokine inhibitor, and a combination of two or more of them;

(2) The cancer vaccine composition for mucosal administration according to (1), further comprising a pharmacologically acceptable acid or a pharmacologically acceptable salt as a second cellular immunity induction promoter;

(3) The cancer vaccine composition for mucosal administration according to (1) or (2), wherein the first cellular immunity induction promoter is a TLR ligand;

(4) The cancer vaccine composition for mucosal administration according to (1) or (2), wherein the first cellular immunity induction promoter is a cyclic dinucleotide;

(5) The cancer vaccine composition for mucosal administration according to (1) or (2), wherein the first cellular immunity induction promoter is an immunomodulatory small molecule drug;

(6) The cancer vaccine composition for mucosal administration according to (1) or (2), wherein the first cellular immunity induction promoter is a cyclooxygenase inhibitor;

(7) The cancer vaccine composition for mucosal administration according to (1) or (2), wherein the first cellular immunity induction promoter is a prostaglandin receptor antagonist and wherein the prostaglandin receptor antagonist is an EP2 receptor antagonist, an EP4 receptor antagonist, a DP receptor antagonist, or an IP receptor antagonist;

(8) The cancer vaccine composition for mucosal administration according to (1) or (2), wherein the first cellular immunity induction promoter is a prostaglandin receptor agonist and wherein the prostaglandin receptor agonist is an EP3 receptor agonist;

(9) The cancer vaccine composition for mucosal administration according to (1) or (2), wherein the first cellular immunity induction promoter is a TSLP production inhibitor;

(10) The cancer vaccine composition for mucosal administration according to (1) or (2), wherein the first cellular immunity induction promoter is an adenylate cyclase inhibitor;

(11) The cancer vaccine composition for mucosal administration according to (1) or (2), wherein the first cellular immunity induction promoter is an omega-3 fatty acid;

(12) The cancer vaccine composition for mucosal administration according to (1) or (2), wherein the first cellular immunity induction promoter is a PPAR agonist and wherein the PPAR agonist is a PPAR-α agonist, a PPAR-δ agonist, or a PPAR-γ agonist;
(13) The cancer vaccine composition for mucosal administration according to (1) or (2), wherein the first cellular immunity induction promoter is a dopamine receptor antagonist and wherein the dopamine receptor antagonist is a D1 receptor antagonist, or a D5 receptor antagonist;
(14) The cancer vaccine composition for mucosal administration according to (1) or (2), wherein the first cellular immunity induction promoter is a dopamine receptor agonist and wherein the dopamine receptor agonist is a D2 receptor agonist, a D3 receptor agonist or a D4 receptor agonist;
(15) The cancer vaccine composition for mucosal administration according to (1) or (2), wherein the first cellular immunity induction promoter is a histamine receptor antagonist and wherein the histamine receptor antagonist is a H1 receptor antagonist or a H2 receptor antagonist;
(16) The cancer vaccine composition for mucosal administration according to (1) or (2), wherein the first cellular immunity induction promoter is a histamine receptor agonist and wherein the histamine receptor agonist is a H1 receptor agonist, a H3 receptor agonist or a H4 receptor agonist;
(17) The cancer vaccine composition for mucosal administration according to (1) or (2), wherein the first cellular immunity induction promoter is a serotonin receptor antagonist and wherein the serotonin receptor antagonist is a 5-HT2 receptor antagonist, a 5-HT4 receptor antagonist, a 5-HT6 receptor antagonist or a 5-HT7 receptor antagonist;
(18) The cancer vaccine composition for mucosal administration according to (1) or (2), wherein the first cellular immunity induction promoter is a serotonin receptor agonist and wherein the serotonin receptor agonist is a 5-HT1 receptor agonist or a 5-HT2 receptor agonist;
(19) The cancer vaccine composition for mucosal administration according to (1) or (2), wherein the first cellular immunity induction promoter is a vasopressin receptor antagonist and wherein the vasopressin receptor antagonist is a V2 receptor antagonist;
(20) The cancer vaccine composition for mucosal administration according to (1) or (2), wherein the first cellular immunity induction promoter is a vasopressin receptor agonist and wherein the vasopressin receptor agonist is a V1 receptor agonist;
(21) The cancer vaccine composition for mucosal administration according to (1) or (2), wherein the first cellular immunity induction promoter is a muscarine receptor antagonist and wherein the muscarine receptor antagonist is a M1 receptor antagonist, a M3 receptor antagonist or a M5 receptor antagonist;
(22) The cancer vaccine composition for mucosal administration according to (1) or (2), wherein the first cellular immunity induction promoter is a muscarine receptor agonist and wherein the muscarine receptor agonist is a M1 receptor agonist, a M2 receptor agonist, a M3 receptor agonist, a M4 receptor agonist or a M5 receptor agonist;
(23) The cancer vaccine composition for mucosal administration according to (1) or (2), wherein the first cellular immunity induction promoter is an adrenalin receptor antagonist and wherein the adrenalin receptor antagonist is an α1 receptor antagonist, a β1 receptor antagonist, a β2 receptor antagonist or a β3 receptor antagonist;
(24) The cancer vaccine composition for mucosal administration according to (1) or (2), wherein the first cellular immunity induction promoter is an adrenalin receptor agonist and wherein the adrenalin receptor agonist is an α1 receptor agonist or an α2 receptor agonist;
(25) The cancer vaccine composition for mucosal administration according to (1) or (2), wherein the first cellular immunity induction promoter is an angiotensin receptor agonist and wherein the angiotensin receptor agonist is an AT2 receptor agonist;
(26) The cancer vaccine composition for mucosal administration according to (1) or (2), wherein the first cellular immunity induction promoter is a GABA receptor agonist and wherein the GABA receptor agonist is a $GABA_B$ receptor agonist;
(27) The cancer vaccine composition for mucosal administration according to (1) or (2), wherein the first cellular immunity induction promoter is a thrombin receptor antagonist and wherein the thrombin receptor antagonist is a PAR-1 receptor antagonist;
(28) The cancer vaccine composition for mucosal administration according to (1) or (2), wherein the first cellular immunity induction promoter is a thrombin receptor agonist and wherein the thrombin receptor agonist is a PAR-1 receptor agonist;
(29) The cancer vaccine composition for mucosal administration according to (1) or (2), wherein the first cellular immunity induction promoter is an opioid receptor agonist;
(30) The cancer vaccine composition for mucosal administration according to (1) or (2), wherein the first cellular immunity induction promoter is a leukotriene receptor antagonist and wherein the leukotriene receptor antagonist is a CysLT1 receptor antagonist or a CysLT2 receptor antagonist;
(31) The cancer vaccine composition for mucosal administration according to (1) or (2), wherein the first cellular immunity induction promoter is a leukotriene receptor agonist and wherein the leukotriene receptor agonist is a BLT receptor agonist;
(32) The cancer vaccine composition for mucosal administration according to (1) or (2), wherein the first cellular immunity induction promoter is a melatonin receptor agonist;
(33) The cancer vaccine composition for mucosal administration according to (1) or (2), wherein the first cellular immunity induction promoter is a somatostatin receptor agonist;
(34) The cancer vaccine composition for mucosal administration according to (1) or (2), wherein the first cellular immunity induction promoter is a cannabinoid receptor agonist;
(35) The cancer vaccine composition for mucosal administration according to (1) or (2), wherein the first cellular immunity induction promoter is a sphingosine-1 phosphate receptor agonist;
(36) The cancer vaccine composition for mucosal administration according to (1) or (2), wherein the first cellular immunity induction promoter is a metabotropic glutamate receptor agonist and wherein the metabotropic glutamate receptor agonist is an mGluR2 receptor agonist, an mGluR3 receptor agonist, an mGluR4 receptor agonist, an mGluR6 receptor agonist, an mGluR7 receptor agonist or an mGluR8 receptor agonist;
(37) The cancer vaccine composition for mucosal administration according to (1) or (2), wherein the first cellular immunity induction promoter is an ADP receptor agonist;
(38) The cancer vaccine composition for mucosal administration according to (1) or (2), wherein the first cellular immunity induction promoter is a phospholipase A2 inhibitor;
(39) The cancer vaccine composition for mucosal administration according to (1) or (2), wherein the first cellular immunity induction promoter is a TGF-β production inhibitor;

(40) The cancer vaccine composition for mucosal administration according to (1) or (2), wherein the first cellular immunity induction promoter is a Th2 cytokine inhibitor;
(41) The cancer vaccine composition for mucosal administration according to (1) or (2), wherein the first cellular immunity induction promoter is a helper peptide;
(42) The cancer vaccine composition for mucosal administration according to (1) or (2), wherein the first cellular immunity induction promoter is a combination of a helper peptide and one or more substances selected from the group consisting of a TLR ligand, a cyclic dinucleotide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor and a Th2 cytokine inhibitor;
(43) The cancer vaccine composition for mucosal administration according to anyone of (1) to (42), which is provided in a form of film;
(44) The cancer vaccine composition for mucosal administration, according to any one of (1) to (42), which is provided in a form of liquid;
(45) The cancer vaccine composition for mucosal administration, according to any one of (1) to (42), which provided is in a form of orally-disintegrating tablet.

In other aspect, the cancer vaccine composition for mucosal administration of the present invention can be used for treating or preventing a cancer. Therefore, the present invention also provides the following embodiments:
(46) A method of treating or preventing a cancer in a subject, comprising mucosally administering to the subject, a therapeutically effective amount of (i) a WT1 peptide and/or a modified WT1 peptide, and (ii) a cellular immunity induction promoter selected from a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, a Th2 cytokine inhibitor, and a combination of two or more of them; and
(47) A method of treating or preventing a cancer in a subject, comprising administering to the subject a therapeutically effective amount of the cancer vaccine composition for mucosal administration according to anyone of (1) to (42), the cancer vaccine film formulation for mucosal administration according to (43), the cancer vaccine liquid formulation for mucosal administration according to (44), or the cancer vaccine orally-disintegrating tablet for mucosal administration according to (45).

In other aspect, the present invention provides a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, a Th2 cytokine inhibitor, or a combination of two or more of them for use as a cellular immunity induction promoter that can enhance the immune response induced by the mucosal administration of a WT1 peptide and/or a modified WT1 peptide. Therefore, the present invention also provides the following aspect:
(48) A TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, a Th2 cytokine inhibitor, or a combination of two or more of them, for use as a cellular immunity induction promoter that can enhance the immune response induced by the mucosal administration of a WT1 peptide and/or a modified WT1 peptide.

The present invention also provides the following embodiments:
(49) A method of inducing cellular immunity, comprising mucosally administering to a subject (i) WT1 peptide and/or modified WT1 peptide and (ii) a first cellular immunity induction accelerator selected from TLR ligand, cyclic dinucleotide, helper peptide, immunomodulatory small molecule drug, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor, Th2 cytokine inhibitor and a combination of two or more kinds of them;

(50) TLR ligand, cyclic dinucleotide, helper peptide, immunomodulatory small molecule drug, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor, Th2 cytokine inhibitor, or a combination of two or more kinds of them, for use in accelerating the induction of cellular immunity by the mucosal administration of WT1 peptide and/or modified WT1 peptide;

(51) A combination of (i) WT1 peptide and/or modified WT1 peptide and (ii) a first cellular immunity induction accelerator selected from TLR ligand, cyclic dinucleotide, helper peptide, immunomodulatory small molecule drug, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor, Th2 cytokine inhibitor and a combination of two or more kinds of them, for use in inducing cellular immunity by the mucosal administration of WT1 peptide and/or modified WT1 peptide;

(52) A combination of (i) WT1 peptide and/or modified WT1 peptide and (ii) a cellular immunity induction accelerator selected from TLR ligand, cyclic dinucleotide, helper peptide, immunomodulatory small molecule drug, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor, Th2 cytokine inhibitor and a combination of two or more kinds of them for use in treating or preventing a cancer, wherein the combination is mucosally administered to a subject; and

(53) Use of (i) WT1 peptide and/or modified WT1 peptide and (ii) a cellular immunity induction accelerator selected from TLR ligand, cyclic dinucleotide, helper peptide, immunomodulatory small molecule drug, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor, Th2 cytokine inhibitor and a combination of two or more kinds of them, for the manufacture of a cancer vaccine composition for mucosal administration.

Since in the cancer vaccine composition of the present invention can be mucosally administrated (particularly, nasal administration, oral mucosal administration including sublingual mucosal administration), it has the following advantages: excellent compliance, for example, non-invasive administration, no pain, and release from fear of injection; patients can administer the cancer vaccine composition by himself/herself since the administration is simple; a risk of accidental infection due to needlestick injury by health care workers can be avoided; in the case of repetitive administration, the ambulatory frequency can be reduced, and this can contribute to the improvement in quality of life of the patient; and medical wastes which necessitate special disposition such as an injection needle are not generated. Further, there is also an advantage that efficacy of the cancer vaccine composition of the present invention is remarkably improved, as compared with administration of the WT1 peptide and/or the modified WT1 peptide alone. Further, there is also an advantage that mucosal administration of the cancer vaccine composition of the present invention can induce stronger cellular immunity as compared with injection administration.

DETAILED DESCRIPTION OF THE INVENTION

First, terms used in the present specification will be defined so that the present invention can be more easily understood. Terms having no definition have the meaning which is normally understood by a person skilled in the art in the fields of, particularly, medicine, pharmacy, immunology, cell biology, biochemistry, polymer chemistry and the like, unless the context requires otherwise.

I. DEFINITION

As used herein, the term "WT1 peptide" means a partial peptide consisting of about 8 to about 15, preferably about 8 to about 12 amino acids. WT1 peptide is a peptide obtained by fragmenting the WT1 protein which is a product of a cancer gene WT1 (Wilm's tumor), and includes Db126 peptide, Db235 peptide and the like. In addition, a partial peptide of WT1 product disclosed in WO 2000/06602, a WT1-derived HLA-A26 binding cancer antigen peptide described in WO 2005/095598, a HLA-A*3303-restricted WT1 peptide described in WO 2007/097358, and a HLA-A*1101-restricted WT1 peptide described in WO 2008/081701 are also included in the "WT1 peptide" of the present invention.

The term "Db126 peptide" means a WT1 peptide consisting of a sequence Arg Met Phe Pro Asn Ala Pro Tyr Leu (SEQ ID No.: 1). The term "Db235 peptide" means a WT1 peptide consisting of a sequence Cys Met Thr Trp Asn Gln Met Asn Leu (SEQ ID No.: 2) (Patent Document 1).

As used herein, the term "modified WT1 peptide" means a peptide in which all or a part of amino acids of a WT1 peptide are modified by substitution, modification or the like.

The modified WT1 peptide includes, for example,
(a) a peptide consisting of an amino acid sequence in which one to several, for example, 1, 2, 3, 4 or 5 amino acids are substituted, deleted or added in an amino acid sequence of a WT1 peptide; and
(b) a peptide consisting of an amino acid sequence in which all or a part of amino acids, for example, one or more, for example, 1, 2, 3, 4, 5, 6, 7, 8, 9, 10, 11 or 12 amino acids are modified in an amino acid sequence of a WT1 peptide.

Examples of "modification" of an amino acid which can be possessed by a modified WT1 peptide include, but not limited to, aliphatic chain addition modification such as alkylation such as acetylation and methylation, glycosylation, hydroxylation, carboxylation, aldehydization, phosphorylation, sulfonylation, formylation, myristoylation, palmitoylation and stearoylation, octanoylation, esterification, amidation, deamidation, disulfide bond formation modification such as cystine modification, glutathione modification and thioglycolic acid modification, glycation, ubiquitination, succinimide formation, glutamylation, prenylation and the like. The modified WT1 peptide may contain a combination of substitution, deletion or addition of one or more amino acids, and modification of one or more amino acids.

As a specific example, Db235m peptide in which a part of Db235 peptide is modified is a modified WT1 peptide consisting of a sequence Cys Tyr Thr Trp Asn Gln Met Asn Leu (SEQ ID No.: 3) (WO 2002/079253), and is included in the modified WT1 peptide in the present invention. A WT1 substitution-type peptide described in WO 2004/026897, a $WT1_{235-243}$ peptide derivative disclosed in WO 2007/063903 A1, and a HLA-A24 restricted cancer antigen peptide disclosed in WO 2003/106682 are also included in the modified WT1 peptide in the present invention.

The WT1 peptide and/or the modified WT1 peptide can be in the free form, or any pharmacologically acceptable salt form, for example, a form of acid salts (acetic acid salt, TFA salt, hydrochloric acid salt, sulfuric acid salt, phosphoric acid salt, lactic acid salt, tartaric acid salt, maleic acid salt, fumaric acid salt, oxalic acid salt, hydrobromic acid salt, succinic acid salt, nitric acid salt, malic acid salt, citric acid salt, oleic acid salt, palmitic acid salt, propionic acid salt, formic acid salt, benzoic acid salt, picric acid salt, benzenesulfonic acid salt, dodecylsulfuric acid salt, methanesulfonic acid salt, p-toluenesulfonic acid salt, glutaric acid salt, a variety of amino acid salts etc.), metal salts (alkali metal salts (e.g. sodium salt, potassium salt), alkaline earth metal salts (e.g. calcium salt, magnesium salt), aluminum salt etc.), or amine salts (triethylamine salt, benzylamine salt, diethanolamine salt, t-butylamine salt, dicyclohexylamine salt, arginine salt, dimethylammonium salt, ammonium salt etc.). A preferable pharmacologically acceptable salt is an acetic acid salt or a TFA salt. The WT1 peptide and/or the modified WT1 peptide which has been synthesized or produced, isolated and purified by a well-known method can be used.

As used herein, the term "cellular immunity induction promoter" means any substance which can enhance the cellular immune response induced by an antigen which is administered together with the substance, as compared with the immune response induced by the antigen without the substance. The cellular immunity induction promoter may include substances specified in the present specification, though it is not limited by the action mechanism by which induction of the cellular immunity is promoted.

As used herein, the term "TLR ligand" means a ligand of a Toll-like receptor (TLR), and includes, for example, ligands of TLR1 to 9. Examples of the TLR ligand include a TLR1/2 ligand, a TLR2 ligand, a TLR2/6 ligand, a TLR2 and Dectin1 ligand, a TLR3 ligand, a TLR4 ligand, a TLR5 ligand, a TLR7 and/or TLR8 ligand, a TLR9 ligand and the like. In a preferable aspect of the present invention, the TLR ligand is one or more selected from the group consisting of a TLR1/2 ligand, a TLR2 ligand, a TLR2/6 ligand, a TLR2 and Dectin1 ligand, a TLR3 ligand, a TLR4 ligand, a TLR7 and/or TLR8 ligand and a TLR9 ligand.

As used herein, the term "TLR1/2 ligand" means a ligand of a heterodimer of a Toll-like receptor (TLR) 1 and a Toll-like receptor $(TLR)_2$, and includes, for example, a triacylated lipoprotein derived from a cell wall of a bacterium and a salt thereof, and these may be an extract, a product or a synthetic product, and are not limited to them.

In a preferable aspect of the present invention, the TLR1/2 ligand is $Pam_3CSK_4$. $Pam_3CSK_4$ has the formula ("Ser-Lys-Lys-Lys-Lys" disclosed as SEQ ID NO: 9):

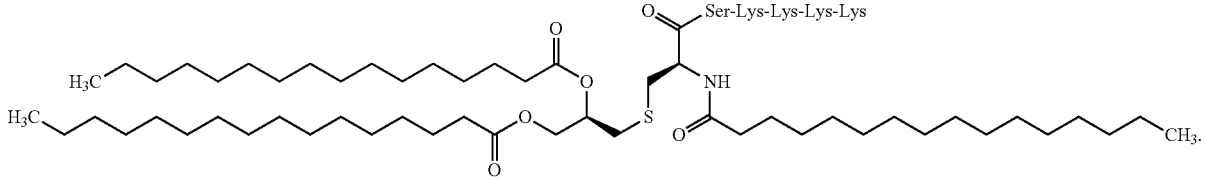

As used herein, the term "TLR2 ligand" means a ligand of TLR2 in a heterodimer of a Toll-like receptor (TLR) 1 and a Toll-like receptor $(TLR)_2$, and TLR2 in a heterodimer of a Toll-like receptor (TLR) 6 and a Toll-like receptor (TLR)₂. The TLR2 ligand includes, for example, lipoteichoic acid, peptide glycans and salts thereof derived from a cell wall of bacteriums, and these may be an extract, a product or a synthetic product, and are not limited to them. In a preferable aspect of the present invention, the TLR2 ligand is a peptide glycan (PGN).

As used herein, the term "TLR2/6 ligand" means a ligand of a heterodimer of a Toll-like receptor (TLR) 2 and a Toll-like receptor (TLR)₆, and includes, for example, diacylated lipoproteins derived from a cell wall of mycoplasma and a salt thereof, and these may be an extract, a product or a synthetic product, and are not limited to them. In a preferable aspect of the present invention, the TLR2/6 ligand is Pam₂CSK₄, MALP-2 and/or FSL-1.

Pam₂CSK₄ is represented by the following formula ("Ser-Lys-Lys-Lys-Lys" disclosed as SEQ ID NO: 9).

plant, particularly, a lipid A derivative, for example, monophosphoryl lipid A, a 3 deacylated monophosphoryl lipid A (3D-MPL) OM174, OM 294 DP or OM 197 MP-Ac DP and the like, alkyl glucosaminide phosphate (AGP), for example, AGP disclosed in WO 98/50399 or U.S. Pat. No. 6,303,347, or a salt of AGP as disclosed in U.S. Pat. No. 6,764,840, and a lipopolysaccharide derived from a *Pantoea* bacterium, a glucopyranosyl lipid, and sodium hyaluronate, but is not limited to them.

In a preferable aspect of the present invention, as the TLR4 ligand, lipopolysaccharides derived from genus *Acetobacter* (e.g. *Acetobacter aceti, Acetobacter xylinum, Acetobacter orientalis* etc.), genus *Zymomonas* (e.g. *Zymomonas mobilis* etc.), genus *Xanthomonas* (e.g. *Xanthomonas campestris* etc.), genus *Enterobacter* (e.g. *Enterobacter cloacae* etc.), and genus *Pantoea* (e.g. *Pantoea agglomerans* etc.) are preferable. Extracts derived from

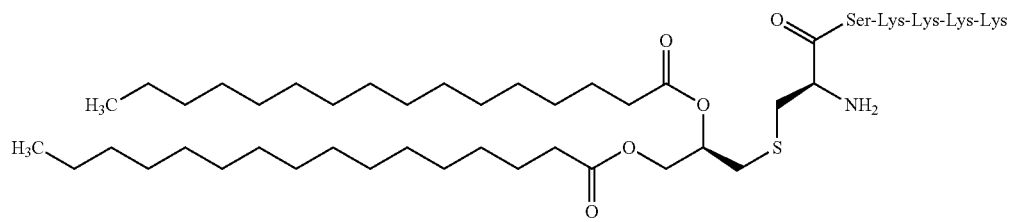

FSL-1 is represented by the following formula ("Gly-Asp-Pro-Lys-His-Pro-Lys-Ser-Phe" disclosed as SEQ ID NO: 10).

these lipopolysaccharides or purified lipopolysaccharides can be used as they are. In addition, for example, lipopolysaccharides (IP-PA1) derived from *Pantoea* agglomerans

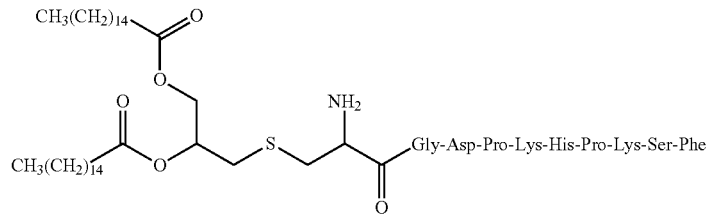

As used herein, the term "TLR2 and Dectin1 ligand" means a ligand of a Toll-like receptor (TLR) 2 and a β1,3-glucan receptor (Dectin1), and includes, for example, a β1,3-glucan derived from a cell wall of a fungus and a salt thereof, and these may be an extract, a product or a synthetic product, and are not limited to them. In a preferable aspect of the present invention, the TLR2 and Dectin1 ligand is Zymosan derived from a yeast cell wall.

As used herein, the term "TLR3 ligand" means a ligand of a Toll-like receptor (TLR)₃, and includes, for example, a double-stranded RNA (dsRNA) derived from a virus and a salt thereof, and these may be an extract, a product or a synthetic product, and are not limited to them. In a preferable aspect of the present invention, the TLR3 ligand is polyinosinic-polycytidylic acid (Poly(I:C)) which is a synthetic product and/or a salt thereof.

As used herein, the term "TLR4 ligand" means a ligand of a Toll-like receptor (TLR)₄, and includes, for example, a lipopolysaccharide (LPS) derived from a bacterium or a can be purchased from Funakoshi Corporation. In addition, in a preferable aspect of the present invention, the TLR4 ligand is a lipopolysaccharide derived from a *Pantoea* bacterium, glucopyranosyl lipid, and/or sodium hyaluronate.

As used herein, the term "TLR5 ligand" means a ligand of a Toll-like receptor (TLR)₅, and includes, for example, flagellin and the like. The TLR5 ligand used in the present invention may be an extract, a product or a synthetic product, and is not limited to them. In a preferable aspect of the present invention, the TLR5 ligand is flagellin.

As used herein, the term "TLR7 and/or TLR8 ligand" means a ligand of a Toll-like receptor (TLR) 7 and/or TLR8, and includes, for example, a single-stranded RNA, imiquimod, resiquimod (R848), TLR7-II and other compounds, for example, loxoribine and bropirimine, but is not limited to them.

In a preferable aspect of the present invention, the TLR7 and/or TLR8 ligand is imiquimod. Imiquimod is 1-(2-methylpropyl)-1H-imidazo[4,5-c]quinoline-4-amine of the formula:

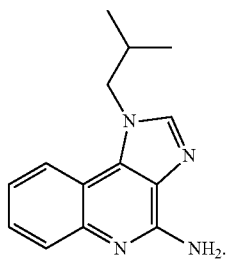 [SMILES: CC(C)Cn1cnc2c(N)nc3ccccc3c21]

and, for example, the characteristics and a production process thereof are described in JP 7-505883 A (Patent Document 2).

In other preferable aspect, the TLR7 and/or TLR8 ligand is resiquimod. Resiquimod is 4-amino-2-(ethoxymethyl)-α,α-dimethyl-1H-imidazo[4,5-c]quinoline-1-ethanol of the formula:

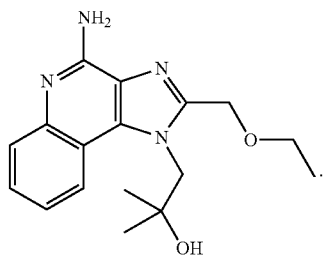 [SMILES: CCOCc1nc2c(N)nc3ccccc3c2n1CC(C)(C)O]

In other preferable aspect, the TLR7 and/or TLR8 ligand is TLR7-II. TLR7-II is represented by the formula:

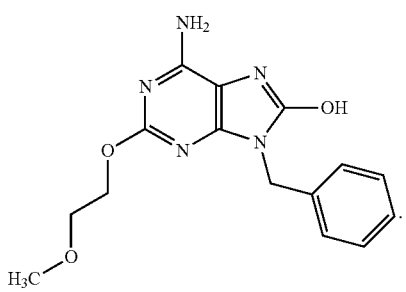 [SMILES: COCCOc1nc(N)c2nc(O)n(Cc3ccccc3)c2n1]

In other preferable aspect, the TLR7 and/or TLR8 ligand is bropirimine. Bropirimine is represented by the formula:

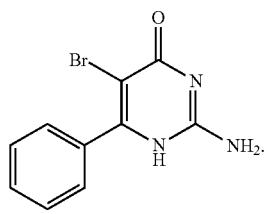 [SMILES: Nc1nc(=O)c(Br)c(-c2ccccc2)[nH]1]

As used herein, the term "TLR9 ligand" means a ligand of a Toll-like receptor (TLR) 9, and includes, for example, ODN1826 and the like. The TLR9 ligand used in the present invention may be an extract, a product or a synthetic product, and is not limited to them. In a preferable aspect of the present invention, the TLR9 ligand is ODN1826.

ODN1826 is an oligodeoxynucleotide consisting of the following sequence (SEQ ID No.: 4).

5'-tccatgacgttcctgacgtt-3'

The Toll-like receptor (TLR) is a family of type I transmembrane proteins which initiates a congenital immune response in which a specific cytokine, a specific chemokine and growth factor participate, by in vivo activation thereof. All TLRs can activate a certain intracellular signal transmission molecule, for example, nuclear factor κB (NF-κB) and a mitogen-activated protein kinase (MAP kinase) or the like, while a specific population of a cytokine and a chemokine which are released seems to be inherent to each TLR. TLR1/2, TLR2/6, TLR4 and TLR5 are widely expressed in general cells such as mucosal epithelial cells, as well as immune cells such as dendritic cell and monocyte. It is known that these receptors recognize a component of a bacterium and promote secretion of inflammatory cytokines (TNF-α, IL-1, and IL-6). TLR4 is also known to promote production of type I interferons (IFNα and IFNβ). TLR3, 7, 8, and 9 include a subfamily of TLR which is present in an endosome fraction or a lysosome fraction of an immune cell (e.g. dendritic cell and monocyte). Specifically, TLR3 is expressed by a wide range of cells such as a dendritic cell and a fibroblast, TLR7 is expressed by a plasma cell-like dendritic cell, and is expressed by a monocyte to a lesser extent, TLR8 is expressed by a monocyte, as well as a monocyte-derived dendritic cell and a myeloid dendritic cell, and TLR9 is expressed by a plasma cell-like dendritic cell. This subfamily mediates recognition of a microorganism nucleic acid (single-stranded RNA, double-stranded RNA, single-stranded DNA etc.). Agonists of TLR3, TLR7 and/or TLR8, and TLR9 stimulate production of a variety of inflammatory cytokines (including, for example, interleukin-6, interleukin-12, TNF-α, and interferon-γ). Such agonists also promote increase in expression of a costimulatory molecule (e.g., CD40, CD80, or CD86), a major histocompatibility complex molecule, and a chemokine receptor. Type I interferons (IFNα and IFNβ) are also produced by a cell upon activation with TLR7 and/or TLR8 agonists.

As used herein, the term "cyclic dinucleotide" means a molecule in which two OH groups of a sugar part of two nucleotides produce an ester for each same phosphoric acid molecule, and thereby nucleotides are cyclized, and an analog thereof, and includes, for example, cyclic di-AMP (c-di-AMP), cyclic di-GMP (c-di-GMP), c-dGpGp, c-dGp-dGp, c-GpAp, c-GpCp, c-GpUp and the like, but is not limited to them. The cyclic dinucleotide activates a dendritic cell or a T cell. Further examples of the cyclic dinucleotide, use of them as an adjuvant, and a process for producing them are described in JP 2007-529531 A (Patent Document 3). In a preferable aspect of the present invention, the cyclic dinucleotide is cyclic di-GMP and/or cyclic di-AMP. The cyclic di-GMP has the formula:

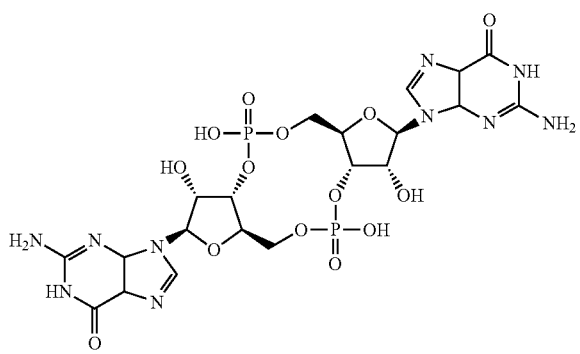 [SMILES: NC1=NC2C(N=CN2[C@@H]2O[C@@H]3COP(=O)(O)O[C@H]4[C@@H](O)[C@H](N5C=NC6C(=O)NC(N)=NC65)O[C@@H]4COP(=O)(O)O[C@H]3[C@H]2O)C(=O)N1]

and a process for synthesizing it is described in Kawai et al., Nucleic Acids Research Suppl. 3: 103-4.

As used herein, the term "helper peptide" means any peptide which activates a helper T cell, and includes, for example, tubercle *bacillus*-derived helper peptide, measles virus-derived helper peptide, hepatitis B virus-derived helper peptide, hepatitis C virus-derived helper peptide, *Chlamydia trachomatis*-derived helper peptide, *Plasmodium falciparum* sporozoite-derived helper peptide, keyhole limpet haemocyanin-derived helper peptide, tetanus toxin-derived helper peptide, pertussis toxin-derived helper peptide, diphtheria toxin-derived helper peptide, cancer cell-derived helper peptide (e.g. WT1$_{332-347}$ helper peptide (described in Japanese Patent No. 4621142 "WT1-derived HLA-DR binding Antigen Peptide"), hWT1$_{35}$ helper peptide, hWT1$_{86}$ helper peptide, hWT1$_{294}$ helper peptide (above three kinds are described in WO 2010/123065 "Cancer Antigen Helper Peptide"), IMA-MMP-001 helper peptide, CEA-006 helper peptide, MMP-001 helper peptide, TGFBI-004 helper peptide, HER-2/neu (aa776-790) helper peptide, AE36 helper peptide, AE37 helper peptide, MET-005 helper peptide, BIR-002 helper peptide), and universal helper analog (e.g. PADRE). In a preferable aspect of the present invention, the helper peptide consists of 10 to 20 amino acids, preferably 12 to 19 amino acids, more preferably 13 to 18 amino acids. In a preferable aspect of the present invention, the helper peptide is Peptide-25, hWT1$_{35}$, or PADRE, or WT1$_{332-347}$ Peptide-25 is a peptide of 15 amino acids consisting of a sequence Phe Gln Asp Ala Tyr Asn Ala Ala Gly Gly His Asn Ala Val Phe (SEQ ID No.: 5), corresponding to amino acid residues 240 to 254 of Ag85B which is one of main proteins secreted by human tubercle *bacillus* (*Mycobacterium tuberculosis*). Further, hWT1$_{35}$ is a peptide of 18 amino acids consisting of a sequence Trp Ala Pro Val Leu Asp Phe Ala Pro Pro Gly Ala Ser Ala Tyr Gly Ser Leu (shown as SEQ ID No.: 6 in the present application), described in WO 2010/123065 "Cancer Antigen Helper Peptide". PADRE is a peptide of 13 amino acids consisting of a sequence D-Ala Lys cyclohexyl-Ala Val Ala Ala Trp Thr Leu Lys Ala Ala D-Ala (shown as SEQ ID No.: 7 in the present application). WT1$_{332-347}$ is a peptide of 16 amino acids consisting of a sequence Lys Arg Tyr Phe Lys Leu Ser His Leu Gln Met His Ser Arg Lys His (shown as SEQ ID No.: 8 in the present application), described in Japanese Patent No. 4621142 "WT1-derived HLA-DR binding Antigen Peptide".

In addition, in the present invention, in place of the aforementioned helper peptide, or in combination therewith, a peptide in which all or a part of amino acids of the helper peptides are modified by substitution, modification, or the like (hereinafter, referred to as "modified helper peptide") can also be used.

The modified helper peptide includes, for example,
(a) a peptide consisting of an amino acid sequence in which one to several, for example, 1, 2, 3, 4 or 5 amino acids are substituted, deleted or added in an amino acid sequence of the original helper peptide; and
(b) a peptide consisting of an amino acid sequence in which all or a part of amino acids, for example, one or more, for example, 1, 2, 3, 4, 5, 6, 7, 8, 9, 10, 11, 12, 13, 14, 15, 16, 17, or 18 amino acids are modified in an amino acid sequence of the original helper peptide.

Examples of the "modification" of an amino acid which can be possessed by the modified helper peptide include, but are not limited to, aliphatic chain addition modification such as acetylation, alkylation such as methylation, glycosylation, hydroxylation, carboxylation, aldehydization, phosphorylation, sulfonylation, formylation, addition of fatty acid such as myristoylation, palmitoylation and stearoylation, octanoylation, esterification, amidation, deamidation, disulfide bond formation modification such as cystine modification, glutathione modification and thioglycolic acid modification, glycation, ubiquitination, succinimide formation, glutamylation, prenylation, and the like. In addition, the modified helper peptide may contain a combination of substitution, deletion or addition of one or more amino acids, and modification of one or more amino acids.

As used herein, the term "cyclooxygenase inhibitor" means a substance which inhibits the function of cyclooxygenase (COX). This is also referred to as "COX inhibitor" hereinafter. As COX inhibitors, there are a COX inhibitor which selectively acts on particular cyclooxygenase (e.g. COX-1 or COX-2), and a COX inhibitor having no selectivity. Examples of COX inhibitors which can be used in the present invention include etodolac, loxoprofen, celecoxib, valdecoxib, parecoxib, lumiracoxib, meloxicam, tenoxicam, diclofenac, mefenamic acid, tolfenamic acid, flufenamic acid, meclofenamic acid, niflumic acid, benzydamine, indobufen, triflusal, tolmetin, fenoprofen, tiaprofenic acid, felbinac, nepafenac, amfenac, pravadoline, zaltoprofen, sulindac, nabumetone, diflunisal, piroxicam, ibuprofen, naproxen, fenoprofen, aspirin, methyl salicylate, salicylamide, salsalate, aloxiprin, tolmetin, indomethacin, proglumetacine, acemetacin, flurbiprofen, pranoprofen, acetaminophen, floctafenine, lornoxicam, tenoxicam, tiaprofenic acid, oxaprozin, ketoprofen, dexketoprofen, dexibuprofen, alminoprofen, ketorolac, mofezolac, phenylbutazone, oxyphenylbutazone, ketophenylbutazone, feprazone, phenbutazone, ethenzamide, tiaramide, tinoridine, epirizole, emorfazone and a derivative thereof, as well as a pharmacologically acceptable salt thereof. In a preferable aspect of the present invention, the COX inhibitor is etodolac and/or loxoprofen.

Loxoprofen is represented by the formula:

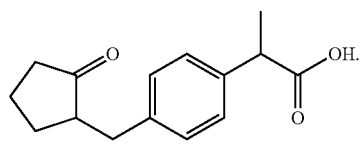 [SMILES: CC(C(=O)O)c1ccc(CC2CCCC2=O)cc1]

As used herein, the term "prostaglandin receptor antagonist" means a substance having the function of preventing prostaglandin from acting on a receptor, and includes, for example, an EP2 receptor antagonist, an EP4 receptor antagonist, a DP receptor antagonist, and an IP receptor antagonist.

As used herein, the term "EP2 receptor antagonist" means a substance having the function of preventing prostaglandin E2 from acting on an EP2 receptor. Examples of the EP2 receptor antagonist include AH6809 and a derivative thereof, as well as a pharmacologically acceptable salt thereof.

AH6809 is represented by the formula:

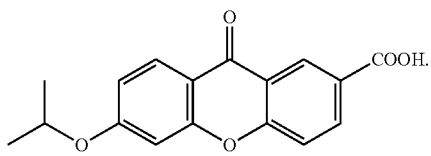 [SMILES: CC(C)Oc1ccc2c(=O)c3cc(C(=O)O)ccc3oc2c1]

As used herein, the term "EP4 receptor antagonist" means a substance having the function of preventing prostaglandin $E_2$ from acting on an EP4 receptor. Examples of the EP4 receptor antagonist include GW627368X and a derivative thereof, as well as a pharmacologically acceptable salt thereof.

GW627368X is represented by the formula:

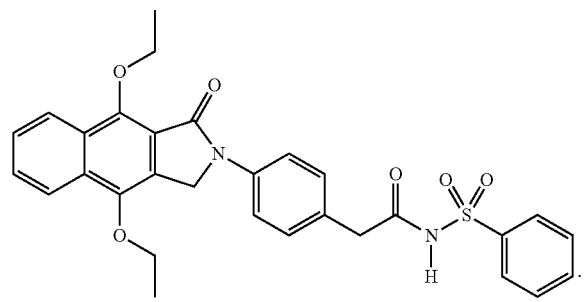 [SMILES: CCOc1c2c(c(OCC)c3ccccc13)C(=O)N(c1ccc(CC(=O)NS(=O)(=O)c3ccccc3)cc1)C2]

As used herein, the term "DP receptor antagonist" means a substance having the function of preventing prostaglandin $D_2$ from acting on a DP receptor. Examples of the DP receptor antagonist include S-5751, BWA868C and a derivative thereof, as well as a pharmacologically acceptable salt thereof.

BWA868C is represented by the formula:

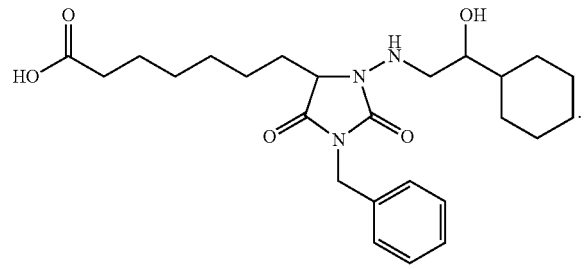 [SMILES: O=C(O)CCCCCCC1C(=O)N(Cc2ccccc2)C(=O)N1NCC(O)C1CCCCC1]

As used herein, the term "IP receptor antagonist" means a substance having the function of preventing prostaglandin $I_2$ from acting on an IP receptor. Examples of the IP receptor antagonist include RO1138452 and a derivative thereof, as well as a pharmacologically acceptable salt thereof.

RO1138452 is represented by the formula:

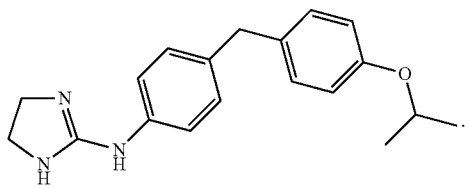 [SMILES: CC(C)Oc1ccc(Cc2ccc(NC3=NCCN3)cc2)cc1]

As used herein, the term "prostaglandin receptor agonist" means a substance having the function of acting on a prostaglandin receptor, and includes, for example, an EP3 receptor agonist.

As used herein, the term "EP3 receptor agonist" means a substance having the function of acting on an EP3 receptor. Examples of the EP3 receptor agonist include sulprostone, GR63799, cloprostenol, ONO-AE-248, carbacyclin, and a derivative thereof, as well as a pharmacologically acceptable salt thereof.

Sulprostone is represented by the formula:

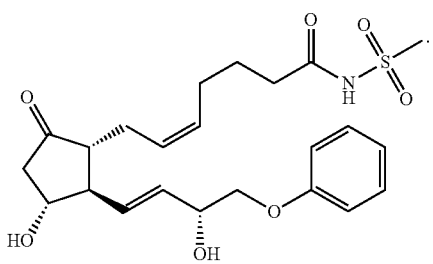 [SMILES: CS(=O)(=O)NC(=O)CCC/C=C\C[C@H]1C(=O)C[C@@H](O)[C@@H]1/C=C/[C@@H](O)COc1ccccc1]

As used herein, the term "TSLP production inhibitor" means a substance having the function of inhibiting production of TSLP. Since a drug which inhibits NF-κB is thought to indirectly inhibit the production of TSLP, it is included in this category. Examples of the TSLP production inhibitor include naringenin, berberine, resveratrol, luteolin, apigenin, chrysoeriol, velutin, rutin, hesperidin, quercetin, daidzein, genistein, noscapine, diindolylmethane, xanthone, parthenolide and a derivative thereof, as well as a pharmacologically acceptable salt thereof.

Berberine is represented by the formula:

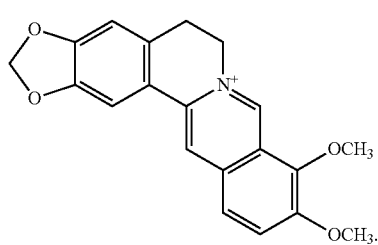 [SMILES: COc1ccc2cc3[n+](cc2c1OC)CCc1cc2c(cc1-3)OCO2]

As used herein, the term "adenylate cyclase inhibitor" means a substance having the function of inhibiting the activity of adenylate cyclase. Examples of the adenylate cyclase inhibitor include 2',5'-dideoxyadenosine, niacin, insulin, and a derivative thereof, as well as a pharmacologically acceptable salt thereof.

2',5'-Dideoxyadenosine is represented by the formula:

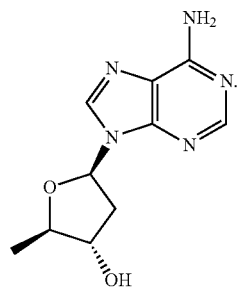 [SMILES: C[C@H]1O[C@@H](n2cnc3c(N)ncnc32)C[C@@H]1O]

As used herein, the term "omega-3 fatty acid" refers to an unsaturated fatty acid having a carbon-carbon double bond at the ω-3 position. Examples of the omega-3 fatty acid include eicosapentaenoic acid, α-linolenic acid, docosahexaenoic acid, and a derivative thereof, as well as a pharmacologically acceptable salt thereof.

Eicosapentaenoic acid is represented by the formula:

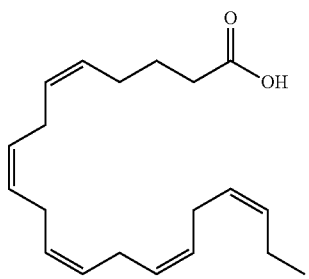

As used herein, the term "PPAR agonist" means a substance having the function of acting on a peroxisome proliferator-activated receptor, and includes, for example, a PPAR-α agonist, a PPAR-δ agonist, and a PPAR-γ agonist.

As used herein, the term "PPAR-α agonist" means a substance having the function of acting on an α type peroxisome proliferator-activated receptor. The term "PPAR-δ agonist" means a substance having the function of acting on a δ type peroxisome proliferator-activated receptor. The term "PPAR-γ agonist" means a substance having the function of acting on a γ type peroxisome proliferator-activated receptor. Examples of the PPAR-α agonist, and/or the PPAR-δ agonist, and/or the PPAR-γ agonist include clofibrate, fenofibrate, bezafibrate, ciprofibrate, etofibrate, telmisartan, oleyl ethanolamide, tetradecylthioacetic acid, troglitazone, pioglitazone, rosiglitazone, balaglitazone, rivoglitazone, ciglitazone, darglitazone, edaglitazone, netoglitazone, indeglitazar, tesaglitazar, muraglitazar, aleglitazar, and a derivative thereof, as well as a pharmacologically acceptable salt thereof.

Clofibrate is represented by the formula:

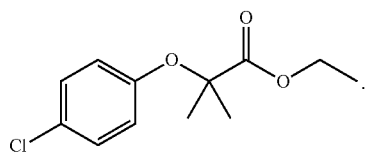 [SMILES: CCOC(=O)C(C)(C)Oc1ccc(Cl)cc1]

As used herein, the term "dopamine receptor antagonist" means a substance having the function of preventing dopamine from acting on a receptor, and includes, for example, a D1 receptor antagonist, and a D5 receptor antagonist.

As used herein, the term "D1 receptor antagonist" means a substance having the function of preventing dopamine from acting on a D1 receptor. Examples of the D1 receptor antagonist include benzazepine, fenoldopam, lorcaserin, SCH23390, SCH39166, LE300 and a derivative thereof, as well as a pharmacologically acceptable salt thereof.

Benzazepine is represented by the formula:

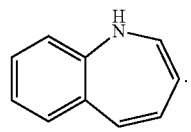

As used herein, the term "D5 receptor antagonist" means a substance having the function of preventing dopamine from acting on a D5 receptor. Examples of the D5 receptor antagonist include SCH39166 and a derivative thereof, as well as a pharmacologically acceptable salt thereof.

SCH39166 is represented by the formula:

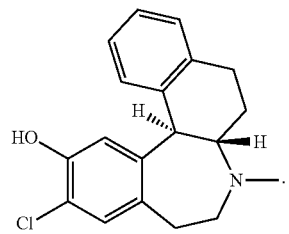 [SMILES: CN1CCc2cc(Cl)c(O)cc2[C@H]2c3ccccc3CC[C@@H]21]

As used herein, the term "dopamine receptor agonist" means a substance having the function of acting on a dopamine receptor, and includes, for example, a D2 receptor agonist, a D3 receptor agonist, and a D4 receptor agonist.

As used herein, the term "D2 receptor agonist" means a substance having the function of acting on a D2 receptor. Examples of the D2 receptor agonist include cabergoline, bromocriptine, pergolide, ropinirole, talipexole, aripiprazole, lurasidone, and a derivative thereof, as well as a pharmacologically acceptable salt thereof.

Ropinirole is represented by the formula:

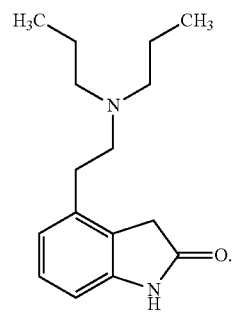

As used herein, the term "D3 receptor agonist" means a substance having the function of acting on a D3 receptor. Examples of the D3 receptor agonist include piribedil, rotigotine, PD1289077, OH-DPAT and a derivative thereof, as well as a pharmacologically acceptable salt thereof.

Rotigotine is represented by the formula:

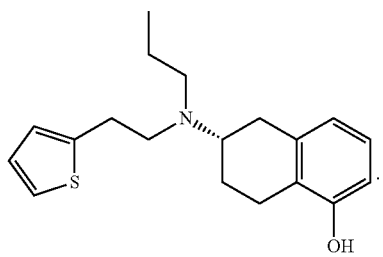 [SMILES: CCCN(CCc1cccs1)[C@H]1CCc2c(O)cccc2C1]

As used herein, the term "D4 receptor agonist" means a substance having the function of acting on a D4 receptor. Examples of the D4 receptor agonist include flibanserin, ABT724, PD168077, CP226269 and a derivative thereof, as well as a pharmacologically acceptable salt thereof.

Flibanserin is represented by the formula:

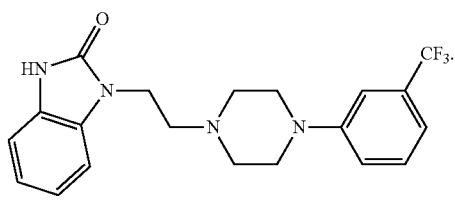 [SMILES: O=c1[nH]c2ccccc2n1CCN1CCN(c2cccc(C(F)(F)F)c2)CC1]

As used herein, the term "histamine receptor antagonist" means a substance having the function of preventing histamine from acting on a receptor, and includes, for example, a H1 receptor antagonist, and a H2 receptor antagonist.

As used herein, the term "H1 receptor antagonist" means a substance having the function of preventing histamine from acting on a H1 receptor. Examples of the H1 receptor antagonist include ketanserin, thonzylamine, mepyramine, tripelenamine, dimethindene, clemastine, bamipine, isothipendyl, chlorphenoxamine, dimetotiazine, chlorpromazine, hydroxyzine, opipramol, betahistine, cinnarizine, levocabastine, antazoline, diphenylpyraline, carbinoxamine, doxylamine, alimemazine, cyclizine, meclozine, levocetirizine, cyproheptadine, phenindamine, triprolidine, azatadine, astemizole, terfenadine, acrivastine, ebastine, desloratadine, rupatadine, bilastine, mizolastine, noberastine, rocastine, temelastine, bepotastine, diphenhydramine, chlorpheniramine, ketotifen, promethazine, cyproheptadine, epinastine, olopatadine, bepotastine, astemizole, emedastine, mequitazine, oxatomide, loratadine, fexofenadine, cetirizine, azelastine, and a derivative thereof, as well as a pharmacologically acceptable salt thereof.

Diphenhydramine is represented by the formula:

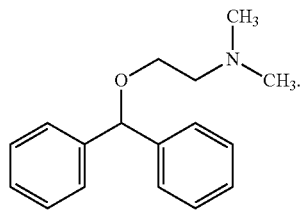 [SMILES: CN(C)CCOC(c1ccccc1)c1ccccc1]

As used herein, the term "H2 receptor antagonist" means a substance having the function of preventing histamine from acting on a H2 receptor. Examples of the H2 receptor antagonist include cimetidine, ranitidine, famotidine, nizatidine, roxatidine, lafutidine, and a derivative thereof, as well as a pharmacologically acceptable salt thereof.

Famotidine is represented by the formula:

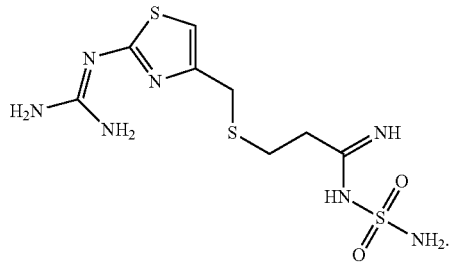 [SMILES: N=C(CCSCc1csc(N=C(N)N)n1)NS(N)(=O)=O]

As used herein, the term "histamine receptor agonist" means a substance having the function of acting on a histamine receptor, and includes, for example, a H1 receptor agonist, a H3 receptor agonist, and a H4 receptor agonist.

As used herein, the term "H1 receptor agonist" means a substance having the function of acting on a H1 receptor. Examples of the H1 receptor agonist include 2-pyridylethylamine, 2-thiazolylethylamine and a derivative thereof, as well as a pharmacologically acceptable salt thereof.

2-Pyridylethylamine is represented by the formula:

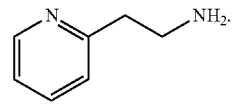

As used herein, the term "H3 receptor agonist" means a substance having the function of acting on a H3 receptor. Examples of the H3 receptor agonist include immethridine, imetit, immepip, α-methylhistamine, proxyfan, and a derivative thereof, as well as a pharmacologically acceptable salt thereof.

Proxyfan is represented by the formula:

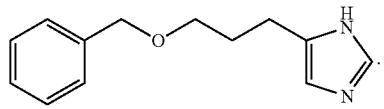 [SMILES: c1ccc(COCCCc2cnc[nH]2)cc1]

As used herein, the term "H4 receptor agonist" means a substance having the function of acting on a H4 receptor. Examples of the H4 receptor agonist include 4-methylhistamine, VUF8430, immepip and a derivative thereof, as well as a pharmacologically acceptable salt thereof.

4-Methylhistamine is represented by the formula:

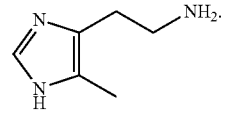

As used herein, the term "serotonin receptor antagonist" means a substance having the function of preventing serotonin from acting on a receptor, and includes, for example, a 5-HT2 receptor antagonist, a 5-HT4 receptor antagonist, a 5-HT6 receptor antagonist, and a 5-HT7 receptor antagonist.

As used herein, the term "5-HT2 receptor antagonist" means a substance having the function of preventing serotonin from acting on a 5-HT2 receptor. Examples of the 5-HT2 receptor antagonist include pizotifen, risperidone, olanzapine, quetiapine, aripiprazole, blonanserin, clozapine, paliperidone, ritanserin, yohimbine, mesulergine, agomelatine, cyclobenzaprine, sarpogrelate, methysergide, ketanserin, and a derivative thereof, as well as a pharmacologically acceptable salt thereof.

Olanzapine is represented by the formula:

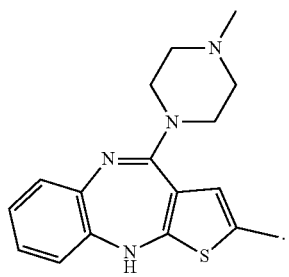 [SMILES: Cc1cc2c(s1)Nc1ccccc1N=C2N1CCN(C)CC1]

As used herein, the term "5-HT4 receptor antagonist" means a substance having the function of preventing serotonin from acting on a 5-HT4 receptor. Examples of the 5-HT4 receptor antagonist include piboserod, GR113808, GR125487, RS39604, SB204070 and a derivative thereof, as well as a pharmacologically acceptable salt thereof.

Piboserod is represented by the formula:

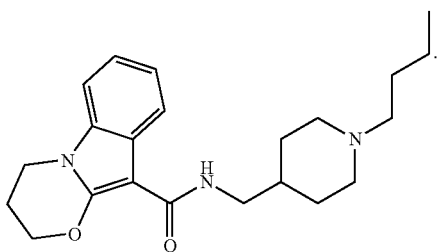 [SMILES: CCCCN1CCC(CNC(=O)c2c3n(c4ccccc24)CCCO3)CC1]

As used herein, the term "5-HT6 receptor antagonist" means a substance having the function of preventing serotonin from acting on a 5-HT6 receptor. Examples of the 5-HT6 receptor antagonist include cerlapirdine, clozapine and a derivative thereof, as well as a pharmacologically acceptable salt thereof.

Cerlapirdine is represented by the formula:

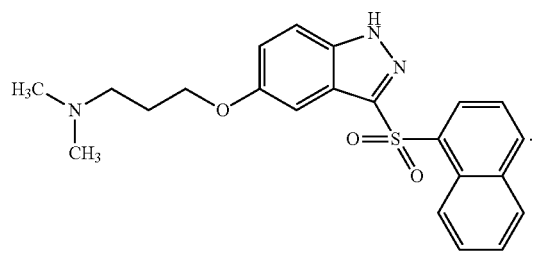 [SMILES: CN(C)CCCOc1ccc2[nH]nc(S(=O)(=O)c3cccc4ccccc34)c2c1]

As used herein, the term "5-HT7 receptor antagonist" means a substance having the function of preventing serotonin from acting on a 5-HT7 receptor. Examples of the 5-HT7 receptor antagonist include lurasidone, metergoline, and a derivative thereof, as well as a pharmacologically acceptable salt thereof.

Metergoline is represented by the formula:

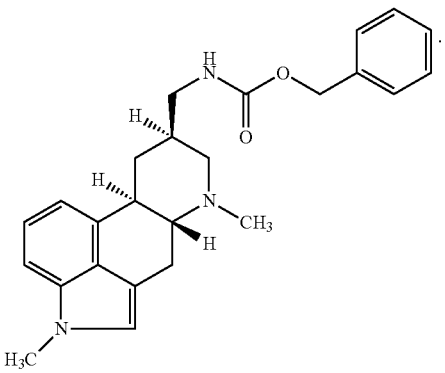 [SMILES: CN1C[C@H](CNC(=O)OCc2ccccc2)C[C@@H]2c3cccc4c3c(cn4C)C[C@H]21]

As used herein, the term "serotonin receptor agonist" means a substance having the function of acting on a serotonin receptor, and includes, for example, a 5-HT1 receptor agonist, and a 5-HT2 receptor agonist.

As used herein, the term "5-HT1 receptor agonist" means a substance having the function of acting on a 5-HT1 receptor. Examples of the 5-HT1 receptor agonist include piclozotan, tandospirone, sumatriptan, zolmitriptan, eletriptan, rizatriptan, naratriptan, almotriptan, frovatriptan, avitriptan, ergotamine, ergot alkaloid, and a derivative thereof, as well as a pharmacologically acceptable salt thereof.

Zolmitriptan is represented by the formula:

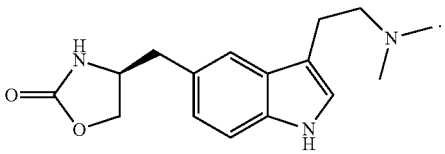 [SMILES: CN(C)CCc1c[nH]c2ccc(C[C@H]3COC(=O)N3)cc12]

As used herein, the term "5-HT2 receptor agonist" means a substance having the function of acting on a 5-HT2 receptor. Examples of the 5-HT2 receptor agonist include α-methyl-5-HT, agomelatine, norfenfluramine, meta-chlorophenylpiperazine and a derivative thereof, as well as a pharmacologically acceptable salt thereof.

Agomelatine is represented by the formula:

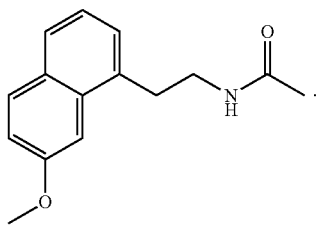 [SMILES: COc1ccc2cccc(CCNC(C)=O)c2c1]

As used herein, the term "vasopressin receptor antagonist" means a substance having the function of preventing vasopressin from acting on a receptor, and includes, for example, a V2 receptor antagonist.

As used herein, the term "V2 receptor antagonist" means a substance having the function of preventing vasopressin from acting on a V2 receptor. Examples of the V2 receptor antagonist include tolvaptan, mozavaptan, conivaptan, lixivaptan, and a derivative thereof, as well as a pharmacologically acceptable salt thereof.

Mozavaptan is represented by the formula:

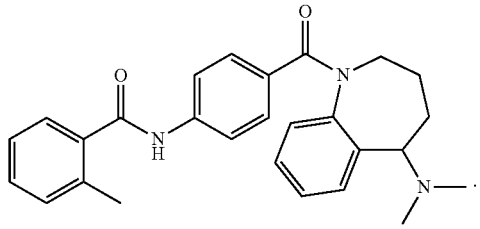 [SMILES: Cc1ccccc1C(=O)Nc1ccc(C(=O)N2CCCC(N(C)C)c3ccccc32)cc1]

As used herein, the term "vasopressin receptor agonist" means a substance having the function of acting on a vasopressin receptor, and includes, for example, a V1 receptor agonist.

As used herein, the term "V1 receptor agonist" means a substance having the function of acting on a V1 receptor. Examples of the V1 receptor agonist include vasopressin, felypressin, desmopressin, lypressin, terlipressin, ornipressin, argipressin, and a derivative thereof, as well as a pharmacologically acceptable salt thereof.

Desmopressin is represented by the formula:

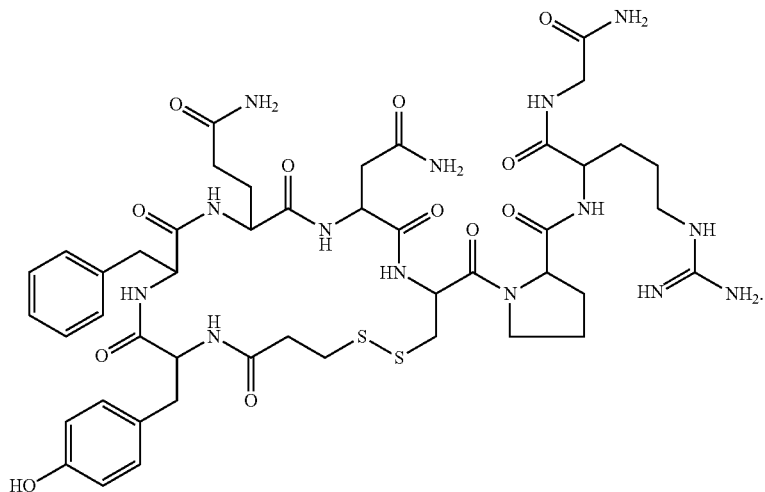 [SMILES: N=C(N)NCCCC(NC(=O)C1CCCN1C(=O)C1CSSCCC(=O)NC(Cc2ccc(O)cc2)C(=O)NC(Cc2ccccc2)C(=O)NC(CCC(N)=O)C(=O)NC(CC(N)=O)C(=O)N1)C(=O)NCC(N)=O]

As used herein, the term "muscarine receptor antagonist" means a substance having the function of preventing acetylcholine from acting on a muscarine receptor, and includes, for example, a M1 receptor antagonist, a M3 receptor antagonist, and a M5 receptor antagonist.

As used herein, the term "M1 receptor antagonist" means a substance having the function of preventing acetylcholine from acting on a M1 receptor. The term "M3 receptor antagonist" means a substance having the function of preventing acetylcholine from acting on a M3 receptor. The term "M5 receptor antagonist" means a substance having the function of preventing acetylcholine from acting on a M5 receptor. Examples of the M1 receptor antagonist, and/or the M3 receptor antagonist, and/or the M5 receptor antagonist include pirenzepine, atropine, trimebutine, piperidolate, oxybutynin, tropicamide, propiverine, tolterodine, solifenacin, darifenacin, imidafenacin, oxyphencyclimine, tiotropium bromide, esoxybutynin, tiquizium, and a derivative thereof, as well as a pharmacologically acceptable salt thereof.

Oxybutynin is represented by the formula:

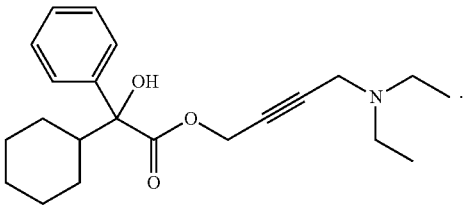 [SMILES: CCN(CC)CC#CCOC(=O)C(O)(c1ccccc1)C1CCCCC1]

As used herein, the term "muscarine receptor agonist" means a substance having the function of acting on a muscarine receptor, and includes, for example, a M1 receptor agonist, a M2 receptor agonist, a M3 receptor agonist, a M4 receptor agonist, and a M5 receptor agonist.

As used herein, the term "M1 receptor agonist" means a substance having the function of acting on a M1 receptor. The term "M2 receptor agonist" means a substance having the function of acting on a M2 receptor. The term "M3 receptor agonist" means a substance having the function of acting on a M3 receptor. The term "M4 receptor agonist" means a substance having the function of acting on a M4 receptor. The term "M5 receptor agonist" means a substance having the function of acting on a M5 receptor. Examples of the M1 receptor agonist, and/or the M2 receptor agonist, and/or the M3 receptor agonist, and/or the M4 receptor agonist, and/or the M5 receptor agonist include acetylcholine, aceclidine, alvameline, talsaclidine, xanomeline, pilocarpine, cevimeline, bethanechol, mazaticol, muscarine, and a derivative thereof, as well as a pharmacologically acceptable salt thereof.

Bethanechol is represented by the formula:

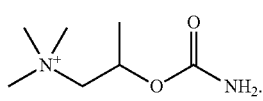

As used herein, the term "adrenalin receptor antagonist" means a substance having the function of preventing adrenalin from acting on a receptor, and includes, for example, an α1 receptor antagonist, a β1 receptor antagonist, a β2 receptor antagonist, and a β3 receptor antagonist.

As used herein, the term "α1 receptor antagonist" means a substance having the function of preventing adrenalin from acting on an α1 receptor. Examples of the α1 receptor antagonist include prazosin, doxazosin, bunazosin, trimazosin, alfuzosin, silodosin, terazosin, tamusulosin, and a derivative thereof, as well as a pharmacologically acceptable salt thereof.

Tamusulosin is represented by the formula:

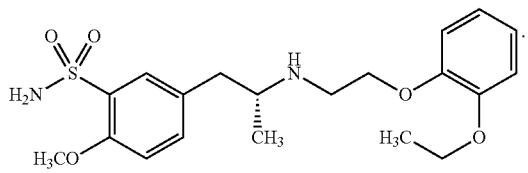 [SMILES: CCOc1ccccc1OCCN[C@H](C)Cc1ccc(OC)c(S(N)(=O)=O)c1]

As used herein, the term "β1 receptor antagonist" means a substance having the function of preventing adrenalin from acting on a β1 receptor. The term "β2 receptor antagonist" means a substance having the function of preventing adrenalin from acting on a β2 receptor. The term "β3 receptor antagonist" means a substance having the function of preventing adrenalin from acting on a β3 receptor. Examples of the receptor antagonist, and/or the β2 receptor antagonist, and/or the β3 receptor antagonist include bopindolol, pindolol, timolol, dichloroisoprenaline, alprenolol, carteolol, indenolol, bunitrolol, penbutolol, propranolol, nadolol, nipradilol, tilisolol, acebutolol, celiprolol, metoprolol, atenolol, bisoprolol, betaxolol, practolol, bevantolol, butoxamine, carvedilol, amosulalol, arotinolol, labetalol, and a derivative thereof, as well as a pharmacologically acceptable salt thereof.

Propranolol is represented by the formula:

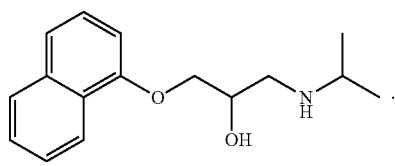 [SMILES: CC(C)NCC(O)COc1cccc2ccccc12]

As used herein, the term "angiotensin receptor agonist" means a substance having the function of acting on an angiotensin receptor, and includes, for example, an AT2 receptor agonist.

As used herein, the term "adrenalin receptor agonist" means a substance having the function of acting on an adrenalin receptor, and includes, for example, an α1 receptor agonist, and an α2 receptor agonist.

As used herein, the term "α1 receptor agonist" means a substance having the function of acting on an α1 receptor. The term "α2 receptor agonist" means a substance having the function of acting on an α2 receptor. Examples of the α1 receptor agonist, and/or the α2 receptor agonist include norepinephrine, norfenefrine, etilefrine, naphazoline, phenylephrine, midodrine, methoxamine, oxedrine, metaraminol, arbutamine, ephedrine, oxymetazoline, tetryzoline, xylometazoline, tramazoline, pseudoephedrine, dipivefrine, amidephrine, methylephedrine, rilmenidine, brimonidine, medetomidine, xylazine, tizanidine, guanfacine, methyldopa, guanabenz, and a derivative thereof, as well as a pharmacologically acceptable salt thereof.

Xylazine is represented by the formula:

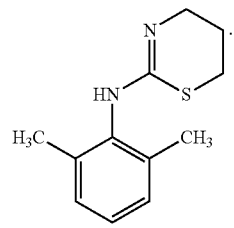

As used herein, the term "angiotensin receptor agonist" means a substance having the function of acting on an angiotensin receptor, and includes, for example, an AT2 receptor agonist.

As used herein, the term "AT2 receptor agonist" means a substance having the function of acting on an AT2 receptor. Examples of the AT2 receptor agonist include novokinin, angiotensin and a derivative thereof, as well as a pharmacologically acceptable salt thereof.

Angiotensin is represented by the formula:

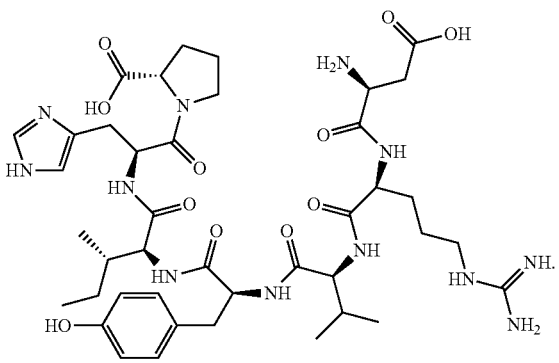 [SMILES: CC[C@H](C)[C@H](NC(=O)[C@H](Cc1ccc(O)cc1)NC(=O)[C@@H](NC(=O)[C@H](CCCNC(=N)N)NC(=O)[C@@H](N)CC(=O)O)C(C)C)C(=O)N[C@@H](Cc1c[nH]cn1)C(=O)N1CCC[C@H]1C(=O)O]

As used herein, the term "GABA receptor agonist" means a substance having the function of acting on a GABA receptor, and includes, for example, a $GABA_B$ receptor agonist.

As used herein, the term "$GABA_B$ receptor agonist" means a substance having the function of acting on a $GABA_B$ receptor. Examples of the $GABA_B$ receptor agonist include baclofen, γ-aminobutyric acid, arbaclofen and a derivative thereof, as well as a pharmacologically acceptable salt thereof.

Baclofen is represented by the formula:

As used herein, the term "thrombin receptor antagonist" means a substance having the function of preventing thrombin from acting on a receptor, and includes, for example, a PAR-1 receptor antagonist.

As used herein, the term "PAR-1 receptor antagonist" means a substance having the function of preventing thrombin from acting on a PAR-1 receptor. Examples of the PAR-1 receptor antagonist include vorapaxar, atopaxar, FR171113, RWJ56110, dabigatran, dabigatran etexilate, melagatran, ximelagatran, hirudin, hirulog, argatroban and a derivative thereof, as well as a pharmacologically acceptable salt thereof.

Vorapaxar is represented by the formula:

As used herein, the term "thrombin receptor agonist" means a substance having the function of acting on a thrombin receptor, and includes, for example, a PAR-1 receptor agonist.

As used herein, the term "PAR-1 receptor agonist" means a substance having the function of acting on a PAR-1 receptor. Examples of the PAR-1 receptor agonist include TRAP-6, TRAP-14, NAT6-NH$_2$ and a derivative thereof, as well as a pharmacologically acceptable salt thereof.

TRAP-6 is represented by the formula:

As used herein, the term "opioid receptor agonist" means a substance having the function of acting on an opioid receptor. Examples of the opioid receptor agonist include trimebutine, alvimopan, morphine, oxycodone, dihydrocodeine, diamorphine, pethidine, pentazocine, buprenorphine, butorphanol, nalbuphine, tilidine, dezocine, meptazinol, tapentadol, naltrexone, methadone, ethylmorphine, hydrocodone, acetyldihydrocodeine, nalorphine, loperamide, remoxipride, opipramol, and a derivative thereof, as well as a pharmacologically acceptable salt thereof.

Buprenorphine is represented by the formula:

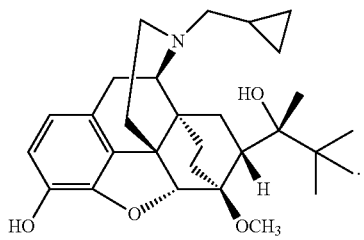 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

As used herein, the term "leukotriene receptor antagonist" means a substance having the function of preventing leukotriene from acting on a receptor, and includes, for example, a CysLT1 receptor antagonist, and a CysLT2 receptor antagonist.

As used herein, the term "CysLT1 receptor antagonist" means a substance having the function of preventing leukotriene from acting on a CysLT1 receptor. The term "CysLT2 receptor antagonist" means a substance having the function of preventing leukotriene from acting on a CysLT2 receptor. Examples of the CysLT1 receptor antagonist, and/or the CysLT2 receptor antagonist include montelukast, zafirlukast, pranlukast, and a derivative thereof, as well as a pharmacologically acceptable salt thereof. Examples of the pharmacologically acceptable salt of montelukast include montelukast sodium and the like.

Montelukast sodium is represented by the formula:

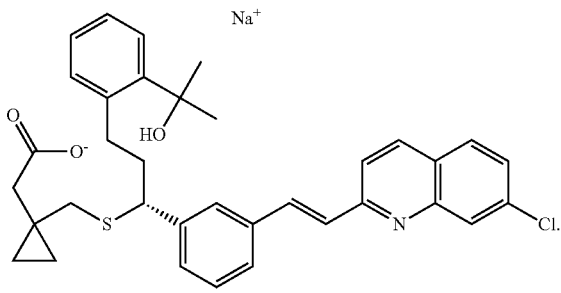 [SMILES: CC(C)(O)c1ccccc1CC[C@@H](SCC1(CC(=O)[O-])CC1)c1cccc(/C=C/c2ccc3ccc(Cl)cc3n2)c1 ; [Na+]]

As used herein, the term "leukotriene receptor agonist" means a substance having the function of acting on a leukotriene receptor, and includes, for example, a BLT receptor agonist.

As used herein, the term "BLT receptor agonist" means a substance having the function of acting on a BLT receptor. Examples of the BLT receptor agonist include leukotriene B4, CAY10583 and a derivative thereof, as well as a pharmacologically acceptable salt thereof.

Leukotriene B4 is represented by the formula:

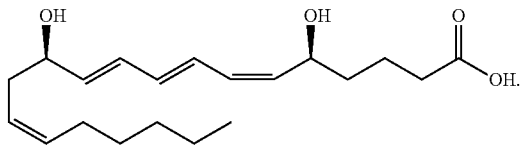 [SMILES: CCCCC/C=C\C[C@@H](O)/C=C/C=C/C=C\[C@@H](O)CCCC(=O)O]

As used herein, the term "ADP receptor agonist" means a substance having the function of acting on an ADP receptor. Examples of the ADP receptor agonist include adenosine diphosphate, and a derivative thereof, as well as a pharmacologically acceptable salt thereof.

Adenosine diphosphate is represented by the formula:

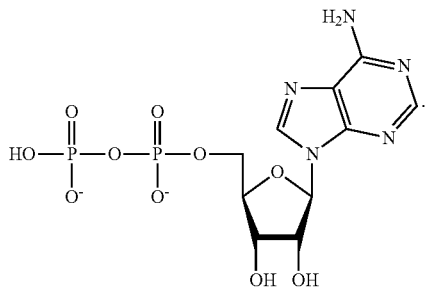

As used herein, the term "melatonin receptor agonist" means a substance having the function of acting on a melatonin receptor. Examples of the melatonin receptor agonist include melatonin, perlapine, tasimelteon, and a derivative thereof, as well as a pharmacologically acceptable salt thereof.

Melatonin is represented by the formula:

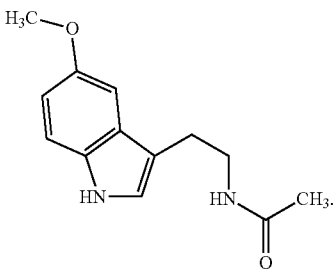 [SMILES: COc1ccc2[nH]cc(CCNC(C)=O)c2c1]

As used herein, the term "somatostatin receptor agonist" means a substance having the function of acting on a somatostatin receptor. Examples of the somatostatin receptor agonist include somatostatin, somatostatin-14, octreotide, and a derivative thereof, as well as a pharmacologically acceptable salt thereof.

Octreotide is represented by the formula:

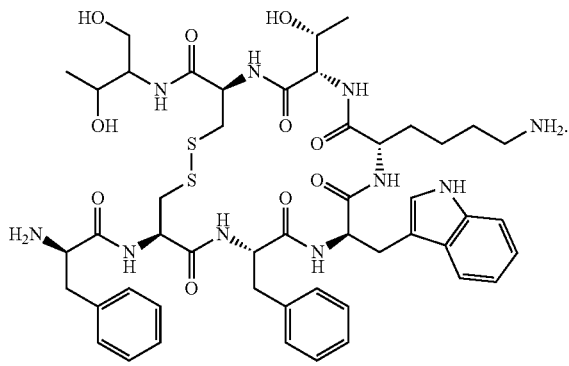 [SMILES: CC(O)C(CO)NC(=O)[C@@H]1CSSC[C@H](NC(=O)[C@H](N)Cc2ccccc2)C(=O)N[C@@H](Cc2ccccc2)C(=O)N[C@H](Cc2c[nH]c3ccccc23)C(=O)N[C@@H](CCCCN)C(=O)N[C@@H]([C@@H](C)O)C(=O)N1]

As used herein, the term "cannabinoid receptor agonist" means a substance having the function of acting on a cannabinoid receptor. Examples of the cannabinoid receptor agonist include dronabinol, nabilone, levonantradol, otenabant, GW833972A, GW405833, and a derivative thereof, as well as a pharmacologically acceptable salt thereof.

Dronabinol is represented by the formula:

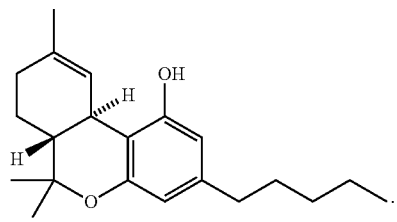 [SMILES: CCCCCc1cc(O)c2c(c1)OC(C)(C)[C@@H]1CCC(C)=C[C@@H]21]

As used herein, the term "sphingosine-1 phosphate receptor agonist" means a substance having the function of acting on a sphingosine-1 phosphate receptor. Examples of the sphingosine-1 phosphate receptor agonist include fingolimod, ponesimod, RPC-1063, ONO-4641, SEW2871, sphingosine-1 phosphate and a derivative thereof, as well as a pharmacologically acceptable salt thereof.

Fingolimod is represented by the formula:

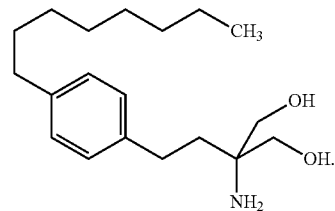

As used herein, the term "metabotropic glutamate receptor agonist" means a substance having the function of acting on a metabotropic glutamate receptor, and includes, for example, an mGluR2 receptor agonist, an mGluR3 receptor agonist, an mGluR4 receptor agonist, an mGluR6 receptor agonist, an mGluR7 receptor agonist, and an mGluR8 receptor agonist.

As used herein, the term "mGluR2 receptor agonist" means a substance having the function of acting on an mGluR2 receptor. The term "mGluR3 receptor agonist" means a substance having the function of acting on an mGluR3 receptor. The term "mGluR4 receptor agonist" means a substance having the function of acting on an mGluR4 receptor. The term "mGluR6 receptor agonist" means a substance having the function of acting on an mGluR6 receptor. The term "mGluR7 receptor agonist" means a substance having the function of acting on an mGluR7 receptor. The term "mGluR8 receptor agonist" means a substance having the function of acting on an mGluR8 receptor. Examples of the mGluR2 receptor agonist, and/or the mGluR3 receptor agonist, and/or the mGluR4 receptor agonist, and/or the mGluR6 receptor agonist, and/or the mGluR7 receptor agonist, and/or the mGluR8 receptor agonist include VU0361737, VU0155041, biphenylindanone A, PBDA, L-AP4, and a derivative thereof, as well as a pharmacologically acceptable salt thereof.

VU0361737 is represented by the formula:

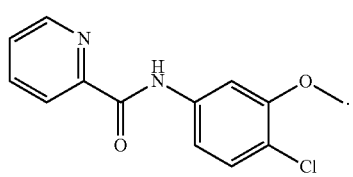 [SMILES: COc1cc(NC(=O)c2ccccn2)ccc1Cl]

As used herein, the term "phospholipase A2 inhibitor" means a substance having the function of inhibiting the activity of phospholipase A2. Examples of the phospholipase A2 inhibitor include glycyrrhizic acid, glycyrrhetic acid, and a derivative thereof, as well as a pharmacologically acceptable salt thereof.

Glycyrrhetic acid is represented by the formula:

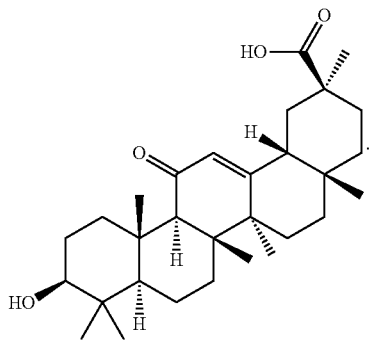

As used herein, the term "TGF-β production inhibitor" means a substance having the function of inhibiting production of TGF-β. Examples of the TGF-β production inhibitor include pirfenidone, tranilast, and a derivative thereof, as well as a pharmacologically acceptable salt thereof.

Pirfenidone is represented by the formula:

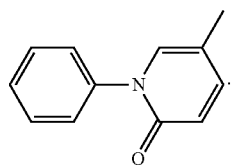

As used herein, the term "Th2 cytokine inhibitor" means a substance having the function of inhibiting production of a Th2 cytokine such as IL-4 and IL-5. Examples of the Th2 cytokine inhibitor include suplatast and a derivative thereof, as well as a pharmacologically acceptable salt thereof. Examples of the pharmacologically acceptable salt of suplatast include suplatast tosylate. In a preferable aspect of the present invention, the Th2 cytokine inhibitor is suplatast tosylate.

Suplatast tosylate is represented by the formula:

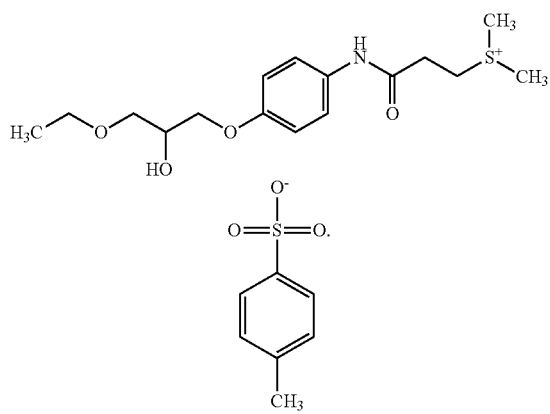

As used herein, the "pharmacologically acceptable acid" as a second cellular immunity induction promoter which can be contained in the composition of the present invention means an acid which has no harmful effect on the subject to which it is administered, and does not impair the pharmacological activity of the ingredients in the composition. In a preferable aspect of the present invention, the pharmacologically acceptable acid is an organic acid, more preferably an organic compound containing carboxyl group or an organic compound containing sulfonate group, more preferably a saturated or an unsaturated straight or a branched fatty acid in which the saturated straight chain part has 8 to 20 carbon atoms, lactic acid, malic acid, salicylic acid, maleic acid, citric acid, or an organic compound containing sulfonate group, more preferably a saturated or unsaturated straight or a branched fatty acid in which the saturated straight chain part has 8 to 16 carbon atoms, lactic acid, malic acid, salicylic acid, maleic acid, citric acid, or an organic compound containing sulfonate group, further preferably a fatty acid selected from the group consisting of decanoic acid, lauric acid, myristic acid, isostearic acid and oleic acid, or lactic acid, salicylic acid, citric acid or methanesulfonic acid.

As used herein, the "pharmacologically acceptable salt" which can be contained in the composition of the present invention means a salt which has no harmful effect on the subject to which it is administered, and does not impair the pharmacological activity of ingredients in the composition, and includes inorganic acid salts (e.g. hydrochloride and phosphate), organic acid salts (e.g. acetate, phthalate, and TFA salt), metal salts (e.g. alkali metal salts such as sodium salt and potassium salt, alkaline earth metal salts such as calcium salt and magnesium salt, aluminum salt etc.), amine salts (e.g. triethylamine salt, benzylamine salt, diethanolamine salt, t-butylamine salt, dicyclohexylamine salt, arginine salt, dimethylammonium salt, ammonium salt etc.), but is not limited to them.

As used herein, the term "immunomodulatory small molecule drug" means a substance which activates or suppresses immune cells such as a T cell, a NK cell, a macrophage and the like, and which does not correspond to any of the aforementioned TLR ligand, cyclic dinucleotide, helper peptide, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor antagonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-β production inhibitor, and Th2 cytokine inhibitor. Examples of the immunomodulatory small molecule drug include bestatin, pidotimod, levamisole, golotimod, forphenicinol, and a derivative thereof, as well as a pharmacologically acceptable salt thereof. Examples of the pharmacologically acceptable salt of levamisole include levamisole hydrochloride.

Bestatin is represented by the formula:

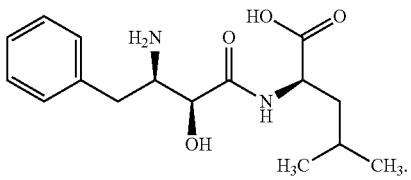 [SMILES: CC(C)C[C@@H](NC(=O)[C@@H](O)[C@H](N)Cc1ccccc1)C(=O)O]

Pidotimod is represented by the formula:

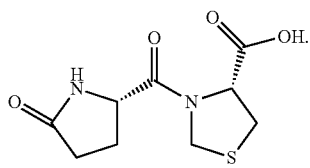 [SMILES: O=C1CC[C@@H](C(=O)N2CSC[C@H]2C(=O)O)N1]

Levamisole hydrochloride is represented by the formula:

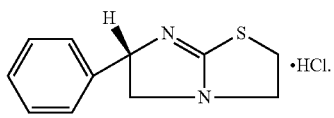 [SMILES: c1ccc([C@H]2CN3CCSC3=N2)cc1]

In the present invention, the immunomodulatory small molecule drug is usually a compound having a molecular weight of less than 1000, preferably less than 500. In a preferable aspect of the present invention, the immunomodulatory small molecule drug is one or more compounds selected from the group consisting of bestatin, pidotimod and levamisole hydrochloride.

As described above, the inventors have found that among a variety of cellular immunity induction promoters, a TLR ligand, a cyclic dinucleotide, a helper peptide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor are particularly suitable for enhancing immune response induced by mucosal administration of the WT1 peptide antigen and/or the modified WT1 peptide antigen. Therefore, in one aspect, the cellular immunity induction promoter of the present invention is one or more substances selected from them. In another aspect, it is the "first cellular immunity induction promoter" of the invention. In a particularly preferable aspect of the present invention, the cellular immunity induction promoter is a combination of a helper peptide and one or more substances selected from the group consisting of a TLR ligand, a cyclic dinucleotide, an immunomodulatory small molecule drug, a cyclooxygenase inhibitor, a prostaglandin receptor antagonist, a prostaglandin receptor agonist, a TSLP production inhibitor, an adenylate cyclase inhibitor, an omega-3 fatty acid, a PPAR agonist, a dopamine receptor antagonist, a dopamine receptor agonist, a histamine receptor agonist, a histamine receptor antagonist, a serotonin receptor agonist, a serotonin receptor antagonist, a vasopressin receptor antagonist, a vasopressin receptor agonist, a muscarine receptor antagonist, a muscarine receptor agonist, an adrenalin receptor antagonist, an adrenalin receptor agonist, an angiotensin receptor agonist, a GABA receptor agonist, a thrombin receptor antagonist, a thrombin receptor agonist, an opioid receptor agonist, an ADP receptor agonist, a leukotriene receptor antagonist, a leukotriene receptor agonist, a melatonin receptor agonist, a somatostatin receptor agonist, a cannabinoid receptor agonist, a sphingosine-1 phosphate receptor agonist, a metabotropic glutamate receptor agonist, a phospholipase A2 inhibitor, a TGF-β production inhibitor, and a Th2 cytokine inhibitor. The induction of cellular immunity can be determined quantitatively by a variety of known methods. Any of those known method, for example, the ELISPOT method described in Examples may be used in this application.

As used herein, non-invasive administration means administration without positively giving physical irritation and/or chemical irritation, preferably without giving physical irritation (e.g. without giving irritation by mucosa peeling treatment, mucosa damaging treatment, and mucosa perforation treatment) to a mucosa.

As used herein, the term "cancer" means a cancer associated with abnormal expression, for example, overexpression of the WT1 gene. Examples of cancer may include hematopoietic tumors and solid cancers. Examples of the hematopoietic tumors associated with abnormal expression of the WT1 gene include, but are not limited to, leukemia such as acute myelocytic leukemia, acute lymphocytic leukemia and chronic myelocytic leukemia, myelodysplastic syndrome, multiple myeloma, as well as malignant lymphoma such as non-Hodgkin's lymphoma. Examples of the solid cancer associated with abnormal expression of the WT1 gene include, but are not limited to, lung cancer, breast cancer, stomach cancer, large intestine/rectum cancer, germ cell cancer, liver cancer, skin cancer, pancreas cancer, bile duct cancer, head and neck squamous cell cancer, thyroid cancer, kidney cancer, bladder cancer, prostate cancer, ovarian cancer, uterine cancer, cervical cancer, bone soft tissue sarcoma, malignant melanoma, malignant mesothelioma, testicular germ cell tumor and malignant glioma.

As used herein, the term "abnormal expression of a gene" means that the expression level of the gene in a cell is increased or decreased remarkably, for example, by 2 times or more such as by 4 times or more, as compared with the other cells of the same tissue. The term "overexpression" means that the abnormal expression is an increase in the expression level. The expression level of a gene can be easily measured using any method well-known in the art.

As used herein, the term "subject" means any animal having the WT1 gene whose immune response can be induced by the mucosal administration of a cancer vaccine composition at a practical stage. Typically, the subject may be a mammal including human, mouse, rat, dog, cat, rabbit, horse, cow, sheep, pig, goat, monkey, and chimpanzee. A particularly preferable subject is human.

As used herein, the term "model animal for immunological evaluation" means a model animal for evaluating the property of a cancer vaccine composition for mucosal administration to induce immunity. Specifically, it means a model animal for evaluating the property of inducing cellular immunity. The model animal for immunological evaluation should be selected in view of compatibility between the antigen in the vaccine composition to be evaluated and the MHC class 1 molecule of the animal. An animal model suitable for evaluating the property of the vaccine composition to induce the cellular immunity should be used. In the case of a vaccine composition containing a HLA-A*24 type MHC restricted class 1 peptide, the property may be evaluated in a BALB/c mouse. In the case of a vaccine composition containing a HLA-A*02 type MHC restricted peptide, the property may be evaluated in a genetically modified mouse by which cellular immunity induction by the HLA-A*02 type MHC restricted peptide can be evaluated. In the case of a vaccine composition containing other HLA type MHC restricted peptide, the property is evaluated in an animal by which cellular immunity induction by the HLA type MHC restricted peptide can be evaluated. In the case of a vaccine composition containing a protein antigen, the property is evaluated in an animal having MHC having compatibility with a class 1 epitope to be used to induce the cellular immunity, among various class 1 epitopes included in the amino acid sequence of the protein antigen. In addition, in the case of a cancer vaccine composition for mucosal administration using Db126 peptide which is compatible with not only HLA-A*02 type but also MHC-H-2Db type, not only a genetically modified mouse by which cellular immunity induction by the HLA-A*0201 type MHC restricted peptide can be evaluated, but also a C57BL/6 mouse which is an animal having MHC-H-2Db type can be used as the model mouse for immunological evaluation.

II. CANCER VACCINE COMPOSITION FOR MUCOSAL ADMINISTRATION

It has been already revealed that WT1 peptides and/or modified WT1 peptides are useful as cancer vaccine (e.g. Patent Document 1).

As used herein, the composition "for mucosal administration" may be provided in any formulation or preparation which is usually used in the mucosal administration such as sublingual administration, nasal administration, buccal administration, rectal administration and vaginal administration, and such formulation may be a semi-solid formulation such as a gel formulation (jelly formulation), a cream formulation, an ointment formulation and a plaster formulation, a liquid formulation, a solid formulation such as a powder formulation, a fine granule formulation, a granule formulation, a film formulation, a tablet formulation, and orally-disintegrating tablets, a spray formulation for mucosa such as an aerosol formulation, an inhalant formulation, or the like. Grouping, definition, a nature, a production process and the like of these formulations are well-known in the art. For example, see Japanese Pharmacopoeia 16th edition.

For example, as a solvent for the liquid formulation, a suitable amount of a solvent such as water, or ethanol, glycerin, propylene glycol or the like can be used, and a liquid formulation can be prepared by dispersing or dissolving ingredients in the solvent.

As a base for the gel formulation (jelly formulation), for example, a carboxyvinyl polymer, a gel base, a fat-free ointment, polyvinylpyrrolidone, polyvinyl alcohol, sodium polyacrylate, carboxymethylcellulose, starch, xanthan gum, karaya gum, sodium alginate, methylcellulose, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, a carboxyvinyl polymer, tragacanth, gum arabic, tara gum, tamarind seed gum, psyllium seed gum, agar, gellan gum, glucomannan, locust bean gum, guar gum, carrageenan, dextrin, dextran, amylose, carboxymethylcellulose potassium, carboxymethylcellulose sodium, carboxymethylcellulose calcium, pullulan, chitosan, sodium carboxymethyl starch, *plantago* testa, galactomannan, Eudragit, casein, alginic acid alkyl ester, gelatin, polyethylene glycol or the like as a hydrogel base can be used. These bases can be dissolved in a solvent to prepare a gel formulation having fluidity or a gel formulation having formability. The solvent is preferably water, while glycerin or propylene glycol can also be used.

Examples of a base for the cream formulation include water/oil type bases such as hydrophilic ointment, vanishing cream and the like; and oil/water type bases such as hydrophilic vaseline, purified lanolin, Aquahole, Eucerin, Neocerin, hydrous lanolin, cold cream, hydrophilic plastibase and the like. These bases can be placed into a fat or oil solvent or water, and stirred with a homogenizer or the like at a high speed to prepare a cream formulation.

Examples of a base for the film formulation include polyvinylpyrrolidone, polyvinyl alcohol, sodium polyacrylate, carboxymethylcellulose, starch, xanthan gum, karaya gum, sodium alginate, methylcellulose, a carboxyvinyl polymer, agar, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, a carboxyvinyl polymer, tragacanth, gum arabic, locust bean gum, guar gum, carrageenan, dextrin, dextran, amylose, carboxymethylcellulose potassium, carboxymethylcellulose sodium, carboxymethylcellulose calcium, pullulan, chitosan, sodium carboxymethyl starch, *plantago* testa, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate/methacrylic acid/methyl methacrylate copolymer, ethyl acrylate/methyl methacrylate copolymer, polyvinylacetal diethylaminoacetate, casein, alginic acid alkyl ester and the like. These bases can be dissolved in water or a polar organic solvent such as ethanol, and after film coating, dried to obtain a film formulation. In one preferable aspect, the vaccine composition for mucosal administration of the present invention is in a form of a film formulation.

For example, the powder formulation, the fine granule formulation, the granule formulation, or the tablet formulation can be prepared using additives such as excipients (e.g., lactose, corn starch, crystalline cellulose, etc.), binders (e.g., hydroxypropylcellulose, gum arabic, etc.), and a suitable amount of a solvent (e.g., water, ethanol, etc.), by mixing the ingredients with stirring, and followed by steps of granulation, drying, compression and the like. If necessary, a lubricant such as magnesium stearate, and a coating agent such as hydroxypropylcellulose, sucrose, and the like may be used.

Examples of a base for the orally-disintegrating tablet (lyophilization type) include polysaccharides such as gelatin and pullulan. In addition, as a molding agent, mannitol, trehalose, sorbitol, glycine or the like may be used. These additives can be dissolved in water, dispensed, and lyophilized to prepare an orally-disintegrating tablet (lyophilization type). In one preferable aspect, the vaccine composition for mucosal administration of the present invention is in a form of an orally-disintegrating tablet.

For example, the aerosol formulation includes, as its content, a liquid formulation, a gel formulation having high fluidity, a cream formulation, fine particles such as powders and the like. Using a spraying device to disperse the content as fine particles of solid or liquid in a gas, the aerosol formulation can be efficiently administered to an administration site, such as an oral mucosa, a nasal mucosa and the like.

The amount of the WT1 peptide and/or the modified WT1 peptide and the cellular immunity induction promoter in the composition of the present invention is not particularly limited. In one aspect, the composition of the present invention contains the WT1 peptide and/or the modified WT1 peptide preferably in an amount of 0.01 to 40% by weight, more preferably 0.1 to 30% by weight based on the total weight of the composition. In one aspect, the composition of the present invention contains the cellular immunity induction promoter preferably in an amount of 0.001 to 30% by weight, more preferably 0.01 to 20% by weight based on the total weight of the composition.

In addition, the composition of the present invention may contain an additive, if necessary. The additive is selected from, for example, isotonizing agents, antiseptics/germicides, antioxidants, resolvents, solubilizers, suspending agents, fillers, pH adjusting agents, stabilizers, absorption promoters, release rate controlling agents, colorants, plasticizers, adhesives and the like, or a combination of two or more of them, depending on the compatibility with the main ingredient of the base, the WT1 peptide and/or the modified WT1 peptide, and the cellular immunity induction promoter, intended administration regimen and the like.

The therapeutically effective amount of the WT1 peptide and/or the modified WT1 peptide may widely vary depending on severity of the disease, age and relative health of the subject and other known factors. In general, satisfactory result may be obtained at a one day dose of about 0.1 µg to 1 g/kg of body weight. The cellular immunity induction promoter is administered simultaneously with the WT1 peptide and/or the modified WT1 peptide or sequentially, and preferably, it is administered simultaneously with the peptide. The effective amount of the cellular immunity induction promoter may widely vary depending on the kind of cellular immunity induction promoter to be used, the presence or absence of other cellular immunity induction promoter and the like, and satisfactory result is obtained at a one day dose of about 0.01 µg to 1 g/kg of body weight. The one day dose may be administered in a single dose or in several divided portions at several times, such as two times or more, for example, two, three, four or five times. The administration interval is appropriately selected, for example, from once per one day, once per 3 days, once per one week, once per 2 weeks, once per one month, once per 3 months, once per 6 months, once per one year, and a longer interval, depending on the state of the patient, severity of the cancer, whether it is for therapeutic purpose or preventive purpose or the like. Generally, for the purpose of treating a patient actually having a severe cancer, the WT1 peptide and/or the modified WT1 peptide are administered at a higher frequency and a higher dose, while for the preventive purpose for a patient having no cancer, the WT1 peptide and/or the modified WT1 peptide are administered at a lower frequency and a lower dose.

The present invention will be explained in more detail and specifically below by way of Examples, but the present invention is not limited to the Examples.

EXAMPLES

Sublingual Liquid Formulation

A liquid formulation having the ingredients of the following Table 1 was produced. Specifically, Db126 peptide (acetic acid salt), the cellular immunity induction promoter, and optionally a pharmacologically acceptable acid, which were weighed at the amounts explicitly described in Table 1, were blended with 4 parts by weight of the additive (DMSO) and the base (saline) to the total of 100 parts by weight, and the materials were mixed to prepare a sublingual liquid formulation.

The Db126 peptide (acetic acid salt) and the Peptide-25 used were chemically synthesized and purified by HPLC. Imiquimod was purchased from Tokyo Chemical Industry Co., Ltd. Cyclic di-GMP (c-di-GMP) and cyclic di-AMP (c-di-AMP) were purchased from Biolog Life Science Institute. $Pam_3CSK_4$ manufactured by InvivoGen, Zymosan manufactured by Nacalai Tesque, Inc., Poly(I:C) manufactured by InvivoGen, *Pantoea* bacterium-derived lipopolysaccharide manufactured by MACROPHI Inc., glucopyranosyl lipid manufactured by InvivoGen (MPLAs), resiquimod (R848) and ODN1826 manufactured by InvivoGen, pidotimod manufactured by Santa Cruz Biotechnology, Inc., bestatin manufactured by Wako Pure Chemical Industries, Ltd., levamisole hydrochloride manufactured by MP Biomedicals, peptide glycan, $Pam_2CSK_4$, and flagellin manufactured by InvivoGen, TLR7-II manufactured by CALBIOCHEM were used, respectively.

The following materials were used.
Imiquimod: manufactured by Tokyo Chemical Industry Co., Ltd., clofibrate: manufactured by LKT Laboratories, Inc., quercetin: manufactured by Cayman Chemical Company, resveratrol (resveratrol (synthetic)): manufactured by Wako Pure Chemical Industries, Ltd., noscapine: manufactured by Wako Pure Chemical Industries, Ltd., 3,3'-diindolylmethane: manufactured by Wako Pure Chemical Industries, Ltd., xanthone: manufactured by Wako Pure Chemical Industries, Ltd., parthenolide: manufactured by Wako Pure Chemical Industries, Ltd., etodolac: manufactured by Wako Pure Chemical Industries, Ltd., loxoprofen (loxoprofen Na): manufactured by Yoshindo Inc., diclofenac (diclofenac sodium): manufactured by Wako Pure Chemical Industries, Ltd., ketoprofen: manufactured by Wako Pure Chemical Industries, Ltd., celecoxib: manufactured by TOCRIS bioscience, docosahexaenoic acid: manufactured by Cayman Chemical Company, 2',5'-dideoxyadenosine: manufactured by BIOMOL International, SCH23390: manufactured by Wako Pure Chemical Industries, Ltd., rotigotine: manufactured by STARNASCENS, GW627368X: manufactured by Cayman Chemical Company, sulprostone: manufactured by Cayman Chemical Company, cloprostenol: manufactured by Wako Pure Chemical Industries, Ltd., BWA868C: manufactured by Cayman Chemical Company, RO1138452: manufactured by Cayman Chemical Company, leukotriene B4: manufactured by Cayman Chemical Company, montelukast (montelukast sodium): manufactured by LG Life Sciences, zileuton: manufactured by Toronto Research Chemicals, Inc., glycyrrhizic acid (dipotassium glycyrrhizinate): manufactured by Wako Pure Chemical Industries, Ltd., pirfenidone: manufactured by TOCRIS bioscience, diphenhydramine (diphenhydramine hydrochloride): manufactured by Wako Pure Chemical Industries, Ltd., famotidine: manufactured by Wako Pure Chemical Industries, Ltd., proxyfan: manufactured by TOCRIS bioscience, azelastine (azelastine hydrochloride): manufactured by LKT Laboratories, Inc., 4-methylhistamine: manufactured by TOCRIS bioscience, olanzapine: manufactured by Wako Pure Chemical Industries, Ltd., zolmitriptan: manufactured by Cipla, tolvaptan: manufactured by Sigma-Aldrich, desmopressin: manufactured by Sigma-Aldrich, pilocarpine (pilocarpine hydrochloride): manufactured by Wako Pure Chemical Industries, Ltd., tamsulosin (tamsulosin hydrochloride): manufactured by Cipla, propranolol (propranolol hydrochloride): manufactured by Wako Pure Chemical Industries, Ltd., xylazine: manufactured by Wako Pure Chemical Industries, Ltd., novokinin: manufactured by Sigma-Aldrich, baclofen: manufactured by Tokyo Chemical Industry Co., Ltd., TRAP-6: manufactured by Bachem, adenosine diphosphate: manufactured by MP Biomedicals, somatostatin-14: manufactured by Bachem, GW405833: manufactured by Sigma-Aldrich, SEW2871: manufactured by Cayman Chemical Company, trimebutine (trimebutine maleate): manufactured by Tokyo Chemical Industry Co., Ltd., loperamide (loperamide hydrochloride): manufactured by Wako Pure Chemical Industries, Ltd., melatonin: manufactured by LKT Laboratories, Inc., L-AP4 (L-2-amino-4-phosphonobutyric acid): manufactured by Wako Pure Chemical Industries, Ltd., and suplatast tosylate: manufactured by TOCRIS bioscience.

Film Formulation

A film formulation having the ingredients of the following Table 1 was produced. Specifically, 46 parts by weight of D-mannitol (manufactured by Roquette), 2.6 parts by weight of polyethylene glycol 400 (manufactured by Wako Pure Chemical Industries, Ltd.), and 150 parts by weight of purified water were blended under ultrasonic agitation. To the mixture were added 41 parts by weight of hydroxypropylcellulose (Nippon Soda Co., Ltd., HPC-SSL), 10 parts by weight of a Db126 peptide (chemically synthesized and HPLC-purified), 0.3 part by weight of Peptide-25 (chemically synthesized and HPLC-purified), and 0.1 part by weight of cellular immunity induction promoters other than helper peptide, and the materials were sufficiently mixed with stirring. The 1/100 amount (2.5 parts by weight) of the solution was added dropwise on a release film made of polyethylene terephthalate, and air-dried and dried under reduced pressure to obtain 1 part by weight of a film formulation. In the mouse immunization test described later, one sheet (10 mg) of the film formulation was administered for each dose per mouse. The cellular immunity induction promoters used were available from the same supplier as described above for the sublingual liquid formulation.

Orally-Disintegrating Tablet

An orally-disintegrating tablet having the ingredients of the following Table 1 was produced. Specifically, 48.6 parts by weight of D-mannitol (manufactured by Roquette) and 41 parts by weight of a water-soluble fish-derived gelatin were added to 400 parts by weight of purified water, and the materials were dissolved at 35° C. To this were added 10 parts by weight of Db126 peptide (chemically synthesized and HPLC-purified), 0.3 part by weight of Peptide-25 (chemically synthesized and HPLC-purified) and 0.1 part by weight of cellular immunity induction promoters other than helper peptide, and the materials were sufficiently mixed with stirring. The 1/100 amount (5 parts by weight) of the solution was added dropwise on aluminum foil and lyophilized to obtain 1 part by weight of an orally-disintegrating tablet. In the mouse immunization test described later, one tablet (10 mg) of the orally-disintegrating tablet was administered for each dose per mouse. The cellular immunity induction promoters used were obtained from the same supplier as described above for the sublingual liquid formulation.

Mouse Immunization Test 1 (Sublingual Administration)

The mouse immunization test was performed using the sublingual liquid formulations, the film formulations and the orally-disintegrating tablets as obtained above. Evaluation of the immunity induction level was performed by the ELISPOT method. Specifically, in the case of one time administration, after the mouse was anesthetized, the liquid formulation, the film formulation or the orally-disintegrating tablet was administered to the sublingual portion and kept the formulation as it was for 2 minutes, and then the mouse was reared for 6 days. In the case of two times administration, the aforementioned operation was repeated 6 days after the first administration. The spleen was isolated 6 days after the last administration, and the antigen-specific cellular immunity induction level was evaluated by the ELISPOT method as described below.

(ELISPOT Method)

A spleen cell suspension was prepared from the isolated spleen. Spleen cells ($3 \times 10^6$ cells/well) and the antigen peptide (100 µM) together with the culturing medium were placed into a well of an ELISPOT plate on which an anti-mouse IFN-γ antibody had been immobilized. The plate was cultured for 20 hours under the conditions of 37° C. and 5% $CO_2$. The number of the spots representing IFN-γ-producing cells (spot number/$3 \times 10^6$ cells) was evaluated by ELISPOT method.

The results of the immunization test are shown in the following Table 1 together with the dose and the number of administrations. Each mouse used was a genetically-modified mouse which can be used to evaluate the cellular immunity inducing ability of a HLA-A*0201 type MHC restricted peptide. For comparison, the results obtained for injectable formulations are also shown in Table 1 (Comparative Examples 2 to 6).

TABLE 1

| | | | | Composition | | | | | Results of immunization (ELISPOT |
|---|---|---|---|---|---|---|---|---|---|
| | Dosage form | Base | Antigen peptide | Cellular immunity induction promoter | | Acid | Dose | Administration | average spot number) |
| Comparative example 1 | liquid formulation | saline | Db126(10) | None | | None | None | 10 µL | 2 times | 12 |
| Example 1 | liquid formulation | saline | Db126(10) | lipopolysaccharide derived from Pantoea bacterium(TLR4 ligand) (0.1) | | None | None | 10 µL | 2 times | 46 |

TABLE 1-continued

|  | Dosage form | Base | Antigen peptide | Cellular immunity induction promoter | Acid | Dose | Administration | Results of immunization (ELISPOT average spot number) |
|---|---|---|---|---|---|---|---|---|
| Example 2 | liquid formulation | saline | Db126(10) | None | PEP(0.3) | 10 μL | 2 times | 33 |
| Example 3 | liquid formulation | saline | Db126(10) | lipopolysaccharide derived from Pantoea bacterium(TLR4 ligand) (0.1) | PEP(0.3) | 10 μL | 2 times | 801 |
| Example 4 | liquid formulation | saline | Db126(10) | lipopolysaccharide derived from Pantoea bacterium(TLR4 ligand) (0.1) | MA (0.1) | 10 μL | 2 times | 904 |
| Example 5 | liquid formulation | saline | Db126(10) | lipopolysaccharide derived from Pantoea bacterium(TLR4 ligand) (0.1) | isostearic acid (0.1) | 10 μL | 2 times | 870 |
| Example 6 | liquid formulation | saline | Db126(10) | lipopolysaccharide derived from Pantoea bacterium(TLR4 ligand) (0.1) | lactic acid (0.1) | 10 μL | 2 times | 850 |
| Example 7 | liquid formulation | saline | Db126(10) | Pam3CSK4(TLR1/2 ligand) (0.1) | PEP(0.3) | 10 μL | 2 times | 152 |
| Example 8 | liquid formulation | saline | Db126(10) | PGN(TLR2 ligand) (0.1) | PEP(0.3) | 10 μL | 2 times | 38 |
| Example 9 | liquid formulation | saline | Db126(10) | Zymosan(ligand for TLR2 and Dectin1) (0.1) | PEP(0.3) | 10 μL | 2 times | 26 |
| Example 10 | liquid formulation | saline | Db126(10) | Pam2CSK4(TLR2/6 ligand) (0.1) | PEP(0.3) | 10 μL | 2 times | 99 |
| Example 11 | liquid formulation | saline | Db126(10) | poly (I:C) (TLR3 ligand) (0.1) | PEP(0.3) | 10 μL | 2 times | 27 |
| Example 12 | liquid formulation | saline | Db126(10) | syn-MPL(TLR4 ligand) (0.1) | PEP(0.3) | 10 μL | 2 times | 103 |
| Example 13 | liquid formulation | saline | Db126(10) | flagellin(TLR5 ligand) (0.1) | PEP(0.3) | 10 μL | 2 times | 27 |
| Example 14 | liquid formulation | saline | Db126(10) | imiquimod(TLR7 and/or TLR8 ligand) (0.1) | PEP(0.3) | 10 μL | 2 times | 74 |
| Example 15 | liquid formulation | saline | Db126(10) | TLR7-II(TLR7 and/or TLR8 ligand) (0.1) | PEP(0.3) | 10 μL | 2 times | 309 |
| Example 16 | liquid formulation | saline | Db126(10) | resiquimod(TLR7 and/or TLR8 ligand) (0.1) | PEP(0.3) | 10 μL | 2 times | 366 |
| Example 17 | liquid formulation | saline | Db126(10) | ODN1826(TLR9 ligand) (0.1) | PEP(0.3) | 10 μL | 2 times | 32 |
| Example 18 | liquid formulation | saline | Db126(10) | c-di-GMP(cyclic dinucleotide) (0.1) | PEP(0.3) | 10 μL | 2 times | 1158 |
| Example 19 | liquid formulation | saline | Db126(10) | c-di-AMP(cyclic dinucleotide) (0.1) | PEP(0.3) | 10 μL | 2 times | 713 |
| Example 20 | liquid formulation | saline | Db126(10) | levamisole HCl(immunomodulatory small molecule drug) (0.1) | PEP(0.3) | 10 μL | 2 times | 74 |
| Example 21 | liquid formulation | saline | Db126(10) | Bestatin (immunomodulatory small molecule drug) (0.1) | PEP(0.3) | 10 μL | 2 times | 35 |
| Example 22 | liquid formulation | saline | Db126(10) | pidotimod (immunomodulatory small molecule drug) (0.1) | PEP(0.3) | 10 μL | 2 times | 7 |
| Example 23 | liquid formulation | saline | Db126(10) | clofibrate(PPAR agonist) (0.1) | PEP(0.3) | 10 μL | 2 times | 110 |
| Example 24 | liquid formulation | saline | Db126(10) | quercetin(TSLP production inhibitor) (0.1) | PEP(0.3) | 10 μL | 2 times | 76 |

TABLE 1-continued

| | Dosage form | Base | Composition Antigen peptide | Cellular immunity induction promoter | Acid | Dose | Administration | Results of immunization (ELISPOT average spot number) |
|---|---|---|---|---|---|---|---|---|
| Example 25 | liquid formulation | saline | Db126(10) | noscapine(TSLP production inhibitor) (0.1) | PEP(0.3) | None | 10 µL | 2 times | 92 |
| Example 26 | liquid formulation | saline | Db126(10) | 3,3'-diindolylmethane (TSLP production inhibitor) (0.1) | PEP(0.3) | None | 10 µL | 2 times | 101 |
| Example 27 | liquid formulation | saline | Db126(10) | xanthone(TSLP production inhibitor) (0.1) | PEP(0.3) | None | 10 µL | 2 times | 95 |
| Example 28 | liquid formulation | saline | Db126(10) | parthenolide(TSLP production inhibitor) (0.1) | PEP(0.3) | None | 10 µL | 2 times | 110 |
| Example 29 | liquid formulation | saline | Db126(10) | loxoprofen(COX inhibitor) (0.1) | PEP(0.3) | None | 10 µL | 2 times | 109 |
| Example 30 | liquid formulation | saline | Db126(10) | etodolac(COX inhibitor) (0.1) | PEP(0.3) | None | 10 µL | 2 times | 85 |
| Example 31 | liquid formulation | saline | Db126(10) | diclofenac(COX inhibitor) (0.1) | PEP(0.3) | None | 10 µL | 2 times | 101 |
| Example 32 | liquid formulation | saline | Db126(10) | ketoprofen(COX inhibitor) (0.1) | PEP(0.3) | None | 10 µL | 2 times | 95 |
| Example 33 | liquid formulation | saline | Db126(10) | celecoxib(COX inhibitor) (0.1) | PEP(0.3) | None | 10 µL | 2 times | 106 |
| Example 34 | liquid formulation | saline | Db126(10) | docosahexaenoic acid(omega-3 fatty acid) (0.1) | PEP(0.3) | None | 10 µL | 2 times | 47 |
| Example 35 | liquid formulation | saline | Db126(10) | 2',5'-dideoxyadenosine (adenylate cyclase inhibitor) (0.1) | PEP(0.3) | None | 10 µL | 2 times | 41 |
| Example 36 | liquid formulation | saline | Db126(10) | SCH23390(dopamine receptor antagonist) (0.1) | PEP(0.3) | None | 10 µL | 2 times | 45 |
| Example 37 | liquid formulation | saline | Db126(10) | rotigotine(dopamine receptor agonist) (0.1) | PEP(0.3) | None | 10 µL | 2 times | 40 |
| Example 38 | liquid formulation | saline | Db126(10) | GW627368X (prostaglandin receptor antagonist) (0.1) | PEP(0.3) | None | 10 µL | 2 times | 120 |
| Example 39 | liquid formulation | saline | Db126(10) | sulprostone (prostaglandin receptor agonist) (0.1) | PEP(0.3) | None | 10 µL | 2 times | 103 |
| Example 40 | liquid formulation | saline | Db126(10) | BWA868C (prostaglandin receptor antagonist) (0.1) | PEP(0.3) | None | 10 µL | 2 times | |
| Example 41 | liquid formulation | saline | Db126(10) | RO1138452 (prostaglandin receptor antagonist) (0.1) | PEP(0.3) | None | 10 µL | 2 times | |
| Example 42 | liquid formulation | saline | Db126(10) | montelukast (leukotriene receptor antagonist) (0.1) | PEP(0.3) | None | 10 µL | 2 times | 56 |
| Example 43 | liquid formulation | saline | Db126(10) | zileuton(leukotriene receptor antagonist) (0.1) | PEP(0.3) | None | 10 µL | 2 times | |
| Example 44 | liquid formulation | saline | Db126(10) | dipotassium glycyrrhizinate (phospholipase A2 inhibitor) (0.1) | PEP(0.3) | None | 10 µL | 2 times | 51 |
| Example 45 | liquid formulation | saline | Db126(10) | pirfenidone(TGF-beta production inhibitor) (0.1) | PEP(0.3) | None | 10 µL | 2 times | 88 |
| Example 46 | liquid formulation | saline | Db126(10) | diphenhydramine (histamine receptor antagonist) (0.1) | PEP(0.3) | None | 10 µL | 2 times | 118 |
| Example 47 | liquid formulation | saline | Db126(10) | famotidine(histamine receptor antagonist) (0.1) | PEP(0.3) | None | 10 µL | 2 times | |

TABLE 1-continued

| | | | Composition | | | | | Results of immunization (ELISPOT |
|---|---|---|---|---|---|---|---|---|
| | Dosage form | Base | Antigen peptide | Cellular immunity induction promoter | Acid | Dose | Administration | average spot number) |
| Example 48 | liquid formulation | saline | Db126(10) | proxyfan(histamine receptor agonist) (0.1) | PEP(0.3) | None | 10 µL | 2 times | 86 |
| Example 49 | liquid formulation | saline | Db126(10) | 4-methylhistamine (histamine receptor agonist) (0.1) | PEP(0.3) | None | 10 µL | 2 times | |
| Example 50 | liquid formulation | saline | Db126(10) | olanzapine(serotonin receptor antagonist) (0.1) | PEP(0.3) | None | 10 µL | 2 times | 85 |
| Example 51 | liquid formulation | saline | Db126(10) | zolmitriptan(serotonin receptor agonist) (0.1) | PEP(0.3) | None | 10 µL | 2 times | 115 |
| Example 52 | liquid formulation | saline | Db126(10) | tolvaptan (vasopressin receptor antagonist) (0.1) | PEP(0.3) | None | 10 µL | 2 times | 52 |
| Example 53 | liquid formulation | saline | Db126(10) | desmopressin (vasopressin receptor agonist) (0.1) | PEP(0.3) | None | 10 µL | 2 times | 57 |
| Example 54 | liquid formulation | saline | Db126(10) | pilocarpine(muscarine receptor agonist) (0.1) | PEP(0.3) | None | 10 µL | 2 times | 46 |
| Example 55 | liquid formulation | saline | Db126(10) | tamsulosin(adrenalin receptor antagonist) (0.1) | PEP(0.3) | None | 10 µL | 2 times | 75 |
| Example 56 | liquid formulation | saline | Db126(10) | propranolol(adrenalin receptor antagonist) (0.1) | PEP(0.3) | None | 10 µL | 2 times | |
| Example 57 | liquid formulation | saline | Db126(10) | xylazine (adrenalin receptor agonist) (0.1) | PEP(0.3) | None | 10 µL | 2 times | 51 |
| Example 58 | liquid formulation | saline | Db126(10) | novokinin (angiotensin receptor agonist) (0.1) | PEP(0.3) | None | 10 µL | 2 times | 48 |
| Example 59 | liquid formulation | saline | Db126(10) | baclofen(GABA receptor agonist) (0.1) | PEP(0.3) | None | 10 µL | 2 times | 42 |
| Example 60 | liquid formulation | saline | Db126(10) | melatonin(melatonin receptor agonist) (0.1) | PEP(0.3) | None | 10 µL | 2 times | 114 |
| Example 61 | liquid formulation | saline | Db126(10) | adenosine diphosphate(ADP receptor agonist) (0.1) | PEP(0.3) | None | 10 µL | 2 times | 54 |
| Example 62 | liquid formulation | saline | Db126(10) | trimebutine(muscarine receptor antagonist) (0.1) | PEP(0.3) | None | 10 µL | 2 times | 93 |
| Example 63 | liquid formulation | saline | Db126(10) | L-AP4(metabotropic glutamate receptor agonist) (0.1) | PEP(0.3) | None | 10 µL | 2 times | 83 |
| Example 64 | liquid formulation | saline | Db126(10) | TRAP-6(thrombin receptor agonist) (0.1) | PEP(0.3) | None | 10 µL | 2 times | 52 |
| Example 65 | liquid formulation | saline | Db126(10) | loperamide(opioid receptor agonist) (0.1) | PEP(0.3) | None | 10 µL | 2 times | 118 |
| Example 66 | liquid formulation | saline | Db126(10) | leukotriene B4(leukotriene receptor agonist) (0.1) | PEP(0.3) | None | 10 µL | 2 times | 53 |
| Example 67 | liquid formulation | saline | Db126(10) | somatostatin-14 (somatostatin receptor agonist) (0.1) | PEP(0.3) | None | 10 µL | 2 times | 57 |

TABLE 1-continued

| | Dosage form | Base | Antigen peptide | Cellular immunity induction promoter | Acid | Dose | Administration | Results of immunization (ELISPOT average spot number) |
|---|---|---|---|---|---|---|---|---|
| Example 68 | liquid formulation | saline | Db126(10) | GW405833 (cannabinoid receptor agonist) (0.1) | PEP(0.3) | None | 10 μL | 2 times | 50 |
| Example 69 | liquid formulation | saline | Db126(10) | SEW2871 (sphingosine-1 phosphate receptor agonist) (0.1) | PEP(0.3) | None | 10 μL | 2 times | 46 |
| Example 70 | liquid formulation | saline | Db126(10) | suplatast tosylate (Th2 cytokine inhibitor) (0.1) | PEP(0.3) | None | 10 μL | 2 times | 48 |
| Example 71 | liquid formulation | saline | Db126(10) | lipopolysaccharide derived from Pantoea bacterium(TLR4 ligand) (0.1) | WT1_35 (0.3) | None | 10 μL | 2 times | 854 |
| Example 72 | liquid formulation | saline | Db126(10) | lipopolysaccharide derived from Pantoea bacterium(TLR4 ligand) (0.1) | WT1_332 (0.3) | None | 10 μL | 2 times | |
| Example 73 | liquid formulation | saline | Db126(10) | lipopolysaccharide derived from Pantoea bacterium(TLR4 ligand) (0.1) | PADRE (0.3) | None | 10 μL | 2 times | 834 |
| Example 74 | film formulation | mannitol/PEG/HPC | Db126(10) | lipopolysaccharide derived from Pantoea bacterium(TLR4 ligand) (0.1) | PEP(0.3) | None | 10 mg | 2 times | 157 |
| Example 75 | film formulation | mannitol/PEG/HPC | Db126(10) | c-di-GMP(cyclic dinucleotide) (0.1) | PEP(0.3) | None | 10 mg | 2 times | 1264 |
| Example 76 | film formulation | mannitol/PEG/HPC | Db126(10) | quercetin(TSLP production inhibitor) (0.1) | PEP(0.3) | None | 10 mg | 2 times | 82 |
| Example 77 | film formulation | mannitol/PEG/HPC | Db126(10) | loxoprofen(COX inhibitor) (0.1) | PEP(0.3) | None | 10 mg | 2 times | 113 |
| Example 78 | orally-disintegrating tablet | mannitol/gelatin | Db126(10) | lipopolysaccharide derived from Pantoea bacterium(TLR4 ligand) (0.1) | PEP(0.3) | None | 10 mg | 2 times | 824 |
| Example 79 | orally-disintegrating tablet | mannitol/gelatin | Db126(10) | c-di-GMP(cyclic dinucleotide) (0.1) | PEP(0.3) | None | 10 mg | 2 times | 1170 |
| Example 80 | orally-disintegrating tablet | mannitol/gelatin | Db126(10) | quercetin(TSLP production inhibitor) (0.1) | PEP(0.3) | None | 10 mg | 2 times | 84 |
| Example 81 | orally-disintegrating tablet | mannitol/gelatin | Db126(10) | loxoprofen(COX inhibitor) (0.1) | PEP(0.3) | None | 10 mg | 2 times | 110 |
| Comparative example 2 | intradermal injection | saline | Db126(0.033) | Montanide ISA51VG(50) | | None | 200 μL | once | 33 |
| Comparative example 3 | intradermal injection | saline | Db126(0.1) | Montanide ISA51VG(50) | | None | 200 μL | once | 28 |
| Comparative example 4 | intradermal injection | saline | Db126(0.33) | Montanide ISA51VG(50) | | None | 200 μL | once | 335 |
| Comparative example 5 | intradermal injection | saline | Db126(1) | Montanide ISA51VG(50) | | None | 200 μL | once | 347 |

TABLE 1-continued

|  | Dosage form | Base | Composition | | Acid | Dose | Administration | Results of immunization (ELISPOT average spot number) |
|---|---|---|---|---|---|---|---|---|
|  |  |  | Antigen peptide | Cellular immunity induction promoter |  |  |  |  |
| Comparative example 6 | intradermal injection | saline | Db126(3.3) | Montanide ISA51VG(50) | None | 200 μL | once | 461 |

A numerical value in parenthesis "( )" is the blending ratio (part(s) by weight) of each ingredient (the same also in Tables below).
HPC: Hydroxypropylcellulose
PEG: Polyethylene glycol 4
PGN: Peptide glycan
poly(I:C): Polyinosinic-polycytidylic acid
syn-MPL: Synthetic monophosphoryl lipid A (glucopyranosyl lipid)
c-di-GMP: Cyclic di-GMP
c-di-AMP: Cyclic di-AMP
Levamisole HCl: Levamisole hydrochloride
PEP: Peptide-25 (SEQ ID No.: 5) (helper peptide)
WT1_35: hWT1$_{35}$ (SEQ ID No.: 6) (helper peptide)
WT1_332: WT1$_{332\text{-}347}$ (SEQ ID No.: 8) (helper peptide)
PADRE: PADRE (SEQ ID No.: 7) (helper peptide)
MA: Myristic acid Nasal Liquid Formulation A liquid formulation having the ingredients of the following Table 2 was produced. Specifically, Db126 peptide (acetic acid salt) and the cellular immunity induction promoter, which were weighed at the amounts explicitly described in Table 2, were blended with 4 parts by weight of the additive (DMSO) and the base (saline) to the total of 100 parts by weight. The materials were mixed to prepare a nasal liquid formulation. The Db126 peptide and the cellular immunity induction promoter were available from the same supplier as described above for the sublingual liquid formulation.

Mouse Immunization Test 2 (Nasal Administration)

The mouse immunization test was performed using the nasal liquid formulation as obtained above. Evaluation of the immunity induction level was performed by the ELISPOT method. Specifically, in the case of one time administration, the liquid formulation was administered by inhalation through a nasal cavity under anesthesia, and then the mouse was reared for 6 days. In the case of two times administration, the aforementioned operation was repeated 6 days after the first administration. The spleen was isolated 6 days after the last administration, and the antigen-specific cellular immunity induction level was evaluated by the ELISPOT method. The ELISPOT method was performed in the same manner as in the mouse immunization test 1.

The results of the immunization test are shown in the following Table 2 together with the dose and the number of administrations. Each mouse used was a genetically-modified mouse which can be used to evaluate the cellular immunity inducing ability of a HLA-A*0201 type MHC restricted peptide. For comparison, the results obtained for injectable formulations are also shown in Table 2 (Comparative Examples 2 to 6).

TABLE 2

|  | Dosage form | Base | Composition | | | Dose | Administration | Results of immunization (ELISPOT average spot number) |
|---|---|---|---|---|---|---|---|---|
|  |  |  | Antigen peptide | Cellular immunity induction promoter | | | | |
| Comparative example 7 | liquid formulation | saline | Db126(10) | None | None | 10 μL | 2 times | 3 |
| Example 82 | liquid formulation | saline | Db126(10) | lipopolysaccharide derived from Pantoea bacterium(TLR4 ligand) (0.1) | None | 10 μL | 2 times | 102 |
| Example 83 | liquid formulation | saline | Db126(10) | c-di-GMP(cyclic dinucleotide) (0.1) | None | 10 μL | 2 times | 1216 |
| Example 84 | liquid formulation | saline | Db126(10) | None | PEP(0.3) | 10 μL | 2 times | 79 |
| Example 85 | liquid formulation | saline | Db126(10) | lipopolysaccharide derived from Pantoea bacterium(TLR4 ligand) (0.1) | PEP(0.3) | 10 μL | 2 times | 202 |
| Example 86 | liquid formulation | saline | Db126(10) | lipopolysaccharide derived from Pantoea bacterium(TLR4 ligand) (0.1) MA(0.1) | PEP(0.3) | 10 μL | 2 times | 243 |
| Example 87 | liquid formulation | saline | Db126(10) | Pam3CSK4(TLR1/2 ligand) (0.1) | PEP(0.3) | 10 μL | 2 times | 270 |
| Example 88 | liquid formulation | saline | Db126(10) | PGN(TLR2 ligand) (0.1) | PEP(0.3) | 10 μL | 2 times | 21 |

TABLE 2-continued

| | Dosage form | Composition | | | Dose | Administration | Results of immunization (ELISPOT average spot number) |
|---|---|---|---|---|---|---|---|
| | | Base | Antigen peptide | Cellular immunity induction promoter | | | |
| Example 89 | liquid formulation | saline | Db126(10) | Zymosan(ligand for TLR2 and Dectin1) (0.1) | PEP(0.3) | 10 µL | 2 times | 156 |
| Example 90 | liquid formulation | saline | Db126(10) | Pam2CSK4(TLR2/6 ligand) (0.1) | PEP(0.3) | 10 µL | 2 times | 68 |
| Example 91 | liquid formulation | saline | Db126(10) | poly(I:C) (TLR3 ligand) (0.1) | PEP(0.3) | 10 µL | 2 times | 194 |
| Example 92 | liquid formulation | saline | Db126(10) | syn-MPL (TLR4 ligand) (0.1) | PEP(0.3) | 10 µL | 2 times | 185 |
| Example 93 | liquid formulation | saline | Db126(10) | flagellin (TLR5 ligand) (0.1) | PEP(0.3) | 10 µL | 2 times | 27 |
| Example 94 | liquid formulation | saline | Db126(10) | imiquimod(TLR7 and/or TLR8 ligand) (0.1) | PEP(0.3) | 10 µL | 2 times | 69 |
| Example 95 | liquid formulation | saline | Db126(10) | TLR7-II(TLR7 and/or TLR8 ligand) (0.1) | PEP(0.3) | 10 µL | 2 times | |
| Example 96 | liquid formulation | saline | Db126(10) | resiquimod(TLR7 and/or TLR8 ligand) (0.1) | PEP(0.3) | 10 µL | 2 times | 333 |
| Example 97 | liquid formulation | saline | Db126(10) | ODN1826(TLR9 ligand) (0.1) | PEP(0.3) | 10 µL | 2 times | 99 |
| Example 98 | liquid formulation | saline | Db126(10) | c-di-GMP(cyclic dinucleotide) (0.1) | PEP(0.3) | 10 µL | 2 times | 1337 |
| Example 99 | liquid formulation | saline | Db126(10) | c-di-AMP(cyclic dinucleotide) (0.1) | PEP(0.3) | 10 µL | 2 times | 929 |
| Example 100 | liquid formulation | saline | Db126(10) | levamisole HCl(immunomodulatory small molecule drug) (0.1) | PEP(0.3) | 10 µL | 2 times | 170 |
| Example 101 | liquid formulation | saline | Db126(10) | Bestatin (immunomodulatory small molecule drug) (0.1) | PEP(0.3) | 10 µL | 2 times | 246 |
| Example 102 | liquid formulation | saline | Db126(10) | pidotimod (immunomodulatory small molecule drug) (0.1) | PEP(0.3) | 10 µL | 2 times | 95 |
| Example 103 | liquid formulation | saline | Db126(10) | clofibrate(PPAR agonist) (0.1) | PEP(0.3) | 10 µL | 2 times | 144 |
| Example 104 | liquid formulation | saline | Db126(10) | quercetin(TSLP production inhibitor) (0.1) | PEP(0.3) | 10 µL | 2 times | 135 |
| Example 105 | liquid formulation | saline | Db126(10) | resveratrol(TSLP production inhibitor) (0.1) | PEP(0.3) | 10 µL | 2 times | 183 |
| Example 106 | liquid formulation | saline | Db126(10) | loxoprofen(COX inhibitor) (0.1) | PEP(0.3) | 10 µL | 2 times | 164 |
| Example 107 | liquid formulation | saline | Db126(10) | docosahexaenoic acid(omega-3 fatty acid) (0.1) | PEP(0.3) | 10 µL | 2 times | |
| Example 108 | liquid formulation | saline | Db126(10) | 2',5'-dideoxyadenosine (adenylate cyclase inhibitor) (0.1) | PEP(0.3) | 10 µL | 2 times | 194 |
| Example 109 | liquid formulation | saline | Db126(10) | SCH23390(dopamine receptor antagonist) (0.1) | PEP(0.3) | 10 µL | 2 times | |
| Example 110 | liquid formulation | saline | Db126(10) | rotigotine(dopamine receptor agonist) (0.1) | PEP(0.3) | 10 µL | 2 times | |
| Example 111 | liquid formulation | saline | Db126(10) | GW627368X (prostaglandin receptor antagonist) 0.1) | PEP(0.3) | 10 µL | 2 times | 190 |
| Example 112 | liquid formulation | saline | Db126(10) | sulprostone (prostaglandin receptor agonist) (0.1) | PEP(0.3) | 10 µL | 2 times | 182 |
| Example 113 | liquid formulation | saline | Db126(10) | cloprostenol (prostaglandin receptor agonist) (0.1) | PEP(0.3) | 10 µL | 2 times | 169 |
| Example 114 | liquid formulation | saline | Db126(10) | montelukast (leukotriene receptor antagonist) (0.1) | PEP(0.3) | 10 µL | 2 times | |

TABLE 2-continued

| | Dosage form | Composition | | | Dose | Administration | Results of immunization (ELISPOT average spot number) |
|---|---|---|---|---|---|---|---|
| | | Base | Antigen peptide | Cellular immunity induction promoter | | | |
| Example 115 | liquid formulation | saline | Db126(10) | dipotassium glycyrrhizinate (phospholipase A2 inhibitor) (0.1) | PEP(0.3) | 10 μL | 2 times | |
| Example 116 | liquid formulation | saline | Db126(10) | pirfenidone(TGF-beta production inhibitor) (0.1) | PEP(0.3) | 10 μL | 2 times | |
| Example 117 | liquid formulation | saline | Db126(10) | diphenhydramine (histamine receptor antagonist) (0.1) | PEP(0.3) | 10 μL | 2 times | |
| Example 118 | liquid formulation | saline | Db126(10) | proxyfan(histamine receptor agonist) (0.1) | PEP(0.3) | 10 μL | 2 times | |
| Example 119 | liquid formulation | saline | Db126(10) | olanzapine(serotonin receptor antagonist) (0.1) | PEP(0.3) | 10 μL | 2 times | |
| Example 120 | liquid formulation | saline | Db126(10) | zolmitriptan (serotonin receptor agonist) (0.1) | PEP(0.3) | 10 μL | 2 times | |
| Example 121 | liquid formulation | saline | Db126(10) | tolvaptan (vasopressin receptor antagonist) (0.1) | PEP(0.3) | 10 μL | 2 times | |
| Example 122 | liquid formulation | saline | Db126(10) | desmopressin (vasopressin receptor agonist) (0.1) | PEP(0.3) | 10 μL | 2 times | |
| Example 123 | liquid formulation | saline | Db126(10) | pilocarpine(muscarine receptor agonist) (0.1) | PEP(0.3) | 10 μL | 2 times | |
| Example 124 | liquid formulation | saline | Db126(10) | famotidine(histamine receptor antagonist) (0.1) | PEP(0.3) | 10 μL | 2 times | 115 |
| Example 125 | liquid formulation | saline | Db126(10) | tamsulosin(adrenalin receptor antagonist) (0.1) | PEP(0.3) | 10 μL | 2 times | |
| Example 126 | liquid formulation | saline | Db126(10) | propranolol (adrenalin receptor antagonist) (0.1) | PEP(0.3) | 10 μL | 2 times | |
| Example 127 | liquid formulation | saline | Db126(10) | xylazine(adrenalin receptor agonist) (0.1) | PEP(0.3) | 10 μL | 2 times | |
| Example 128 | liquid formulation | saline | Db126(10) | novokinin(angiotensin receptor agonist) (0.1) | PEP(0.3) | 10 μL | 2 times | |
| Example 129 | liquid formulation | saline | Db126(10) | baclofen(GABA receptor agonist) (0.1) | PEP(0.3) | 10 μL | 2 times | |
| Example 130 | liquid formulation | saline | Db126(10) | melatonin(melatonin receptor agonist) (0.1) | PEP(0.3) | 10 μL | 2 times | |
| Example 131 | liquid formulation | saline | Db126(10) | adenosine diphosphate(ADP receptor agonist) (0.1) | PEP(0.3) | 10 μL | 2 times | |
| Example 132 | liquid formulation | saline | Db126(10) | trimebutine(muscarine receptor antagonist) (0.1) | PEP(0.3) | 10 μL | 2 times | |
| Example 133 | liquid formulation | saline | Db126(10) | L-AP4(metabotropic glutamate receptor agonist) (0.1) | PEP(0.3) | 10 μL | 2 times | |
| Example 134 | liquid formulation | saline | Db126(10) | lipopolysaccharide derived from Pantoea bacterium(TLR4 ligand) (0.1) | WT1_35 (0.3) | 10 μL | 2 times | 234 |
| Example 135 | liquid formulation | saline | Db126(10) | TRAP-6(thrombin receptor agonist) (0.1) | PEP(0.3) | 10 μL | 2 times | |
| Example 136 | liquid formulation | saline | Db126(10) | loperamide(opioid receptor agonist) (0.1) | PEP(0.3) | 10 μL | 2 times | |

TABLE 2-continued

| | Dosage form | Composition | | | Dose | Administration | Results of immunization (ELISPOT average spot number) |
|---|---|---|---|---|---|---|---|
| | | Base | Antigen peptide | Cellular immunity induction promoter | | | |
| Example 137 | liquid formulation | saline | Db126(10) | leukotriene B4(leukotriene receptor agonist) (0.1) | PEP(0.3) | 10 μL | 2 times | |
| Example 138 | liquid formulation | saline | Db126(10) | somatostatin-14 (somatostatin receptor agonist) (0.1) | PEP(0.3) | 10 μL | 2 times | |
| Example 139 | liquid formulation | saline | Db126(10) | GW405833 (cannabinoid receptor agonist) (0.1) | PEP(0.3) | 10 μL | 2 times | |
| Example 140 | liquid formulation | saline | Db126(10) | SEW2871 (sphingosine-1 phosphate receptor agonist) (0.1) | PEP(0.3) | 10 μL | 2 times | |
| Example 141 | liquid formulation | saline | Db126(10) | suplatast tosylate(Th2 cytokine inhibitor) (0.1) | PEP(0.3) | 10 μL | 2 times | |
| Example 142 | liquid formulation | saline | Db126(10) | lipopolysaccharide derived from Pantoea bacterium(TLR4 ligand) (0.1) | WT1_332 (0.3) | 10 μL | 2 times | |
| Example 143 | liquid formulation | saline | Db126(10) | lipopolysaccharide derived from Pantoea bacterium(TLR4 ligand) (0.1) | PADRE (0.3) | 10 μL | 2 times | 225 |
| Comparative example 2 | intradermal injection | saline | Db126(0.033) | Montanide ISA51VG(50) | | 200 μL | once | 33 |
| Comparative example 3 | intradermal injection | saline | Db126(0.1) | Montanide ISA51VG(50) | | 200 μL | once | 28 |
| Comparative example 4 | intradermal injection | saline | Db126(0.33) | Montanide ISA51VG(50) | | 200 μL | once | 335 |
| Comparative example 5 | intradermal injection | saline | Db126(1) | Montanide ISA51VG(50) | | 200 μL | once | 347 |
| Comparative example 6 | intradermal injection | saline | Db126(3.3) | Montanide ISA51VG(50) | | 200 μL | once | 461 |

Intradermal Injectable Formulation

An intradermal injectable formulation having the ingredients of the following Table 3 was prepared. Specifically, Db126 peptide (acetic acid salt) and Montanide ISA51VG (Freund Corporation) as an adjuvant, which were weighed at the amounts explicitly described in Table 3, were blended with 0.5 part by weight of the additive (DMSO) and the base (saline) to the total of 100 parts by weight, and the materials were mixed to prepare an injectable formulation. The Db126 peptide was available from the same supplier as described above for the sublingual liquid formulation.

Mouse Immunization Test 3 (Intradermal Injection)

The mouse immunization test was performed using the intradermal injectable formulation as obtained above. Evaluation of the immunity induction level was performed by the ELISPOT method. Specifically, 200 μL of the injectable formulation was intradermally administered to the back of the mouse, and the mouse was then kept for 6 days. The spleen was isolated 6 days after the administration, and the antigen-specific cellular immunity induction level was assessed by the ELISPOT method. The administration was performed once, and each mouse used was a genetically-modified mouse which can be used to evaluate the cellular immunity inducing ability of a HLA-A*0201 type MHC restricted peptide. The ELISPOT method was performed in the same manner as in the mouse immunization test 1. The results of the immunization test are shown in the following Table 3.

TABLE 3

| | Composition | | | | Dose | Administration | Results of immunization (ELISPOT average spot number) |
|---|---|---|---|---|---|---|---|
| | Base | Antigen peptide | Cellular immunity induction promoter | | | | |
| Comparative Example 2 | Saline | Db126(0.033) | Montanide ISA51VG(50) | | 200 μL | Once | 33 |
| Comparative Example 3 | Saline | Db126(0.1) | Montanide ISA51VG(50) | | 200 μL | Once | 28 |

TABLE 3-continued

|  | Composition | | | | Results of immunization (ELISPOT |
|---|---|---|---|---|---|
|  | Base | Antigen peptide | Cellular immunity induction promoter | Dose | Administration | average spot number) |
| Comparative Example 4 | Saline | Db126(0.33) | Montanide ISA51VG(50) | 200 µL | Once | 335 |
| Comparative Example 5 | Saline | Db126(1) | Montanide ISA51VG(50) | 200 µL | Once | 347 |
| Comparative Example 6 | Saline | Db126(3.3) | Montanide ISA51VG(50) | 200 µL | Once | 461 |

A cancer vaccine composition for mucosal administration comprising WT1 peptide and/or modified WT1 peptide and a first cellular immunity induction promoter was administered in sublingual (Table 1) or nasal (Table 2) route, and an efficacy of the first cellular immunity induction promoter was evaluated.

As a result, a cellular immunity induction promoter selected from TLR ligand, cyclic dinucleotide, helper peptide, immunomodulatory small molecule drug, cyclooxygenase inhibitor, prostaglandin receptor antagonist, prostaglandin receptor agonist, TSLP production inhibitor, adenylate cyclase inhibitor, omega-3 fatty acid, PPAR agonist, dopamine receptor antagonist, dopamine receptor agonist, histamine receptor agonist, histamine receptor antagonist, serotonin receptor agonist, serotonin receptor antagonist, vasopressin receptor antagonist, vasopressin receptor agonist, muscarine receptor antagonist, muscarine receptor agonist, adrenalin receptor antagonist, adrenalin receptor agonist, angiotensin receptor agonist, GABA receptor agonist, thrombin receptor agonist, opioid receptor agonist, ADP receptor agonist, leukotriene receptor antagonist, leukotriene receptor agonist, melatonin receptor agonist, somatostatin receptor agonist, cannabinoid receptor agonist, sphingosine-1 phosphate receptor agonist, metabotropic glutamate receptor agonist, phospholipase A2 inhibitor, TGF-beta production inhibitor, Th2 cytokine inhibitor and a combination of two or more kinds of them, was preferable.

Preferably, a first cellular immunity induction promoter selected from TLR ligand, cyclic dinucleotide, immunomodulatory small molecule drug, cyclooxygenase inhibitor, TSLP production inhibitor, prostaglandin receptor antagonist, prostaglandin receptor agonist, PPAR agonist, TGF-beta production inhibitor, histamine receptor agonist, histamine receptor antagonist, serotonin receptor agonist, serotonin receptor antagonist, muscarine receptor antagonist, adrenalin receptor antagonist, opioid receptor agonist, melatonin receptor agonist, metabotropic glutamate receptor agonist and a combination of two or more kinds of them, as well as a combination of a helper peptide with the first cellular immunity induction promoter other than helper peptide were effective.

Regarding sublingual administration, more preferably, a first cellular immunity induction promoter selected from TLR4 ligand, TLR1/2 ligand, TLR2/6 ligand, TLR7 and/or TLR8 ligand, cyclic dinucleotide, immunomodulatory small molecule drug, cyclooxygenase inhibitor, TSLP production inhibitor, prostaglandin receptor antagonist, prostaglandin receptor agonist, PPAR agonist, TGF-beta production inhibitor, histamine receptor agonist, histamine receptor antagonist, serotonin receptor agonist, serotonin receptor antagonist, muscarine receptor antagonist, adrenalin receptor antagonist, opioid receptor agonist, melatonin receptor agonist, metabotropic glutamate receptor agonist and a combination of two or more kinds of them, as well as a combination of a helper peptide with the first cellular immunity induction promoter other than helper peptide were effective.

Regarding nasal administration, further preferably, a first cellular immunity induction promoter selected from TLR4 ligand, TLR1/2 ligand, ligand for TLR2 and Dectin1, TLR3 ligand, TLR7 and/or TLR8 ligand, cyclic dinucleotide, immunomodulatory small molecule drug, cyclooxygenase inhibitor, TSLP production inhibitor, prostaglandin receptor antagonist, prostaglandin receptor agonist, PPAR agonist, TGF-beta production inhibitor, histamine receptor agonist, histamine receptor antagonist, serotonin receptor agonist, serotonin receptor antagonist, muscarine receptor antagonist, adrenalin receptor antagonist, opioid receptor agonist, melatonin receptor agonist, metabotropic glutamate receptor agonist and a combination of two or more kinds of them, as well as a combination of a helper peptide with the first cellular immunity induction promoter other than helper peptide were effective.

It was also confirmed that the induction of cellular immunity is accelerated by the addition of a pharmacologically acceptable acid or a pharmacologically acceptable salt thereof as a second cellular immunity induction promoter.

From the viewpoint of safety, a sublingual administration is preferable rather than a nasal administration. However, the strong induction of immunity was also confirmed when a film formulation or an orally-disintegrating tablet, which is a preferable form in view of convenient administration and storage stability, was used.

As shown in Tables 1 and 2, the mucosal administration of the cancer vaccine composition comprising the WT1 peptide and/or modified WT1 peptide can induce cellular immune response equivalent to or stronger than that induced by injection. Current Opinion in Immunology 2008, 20: 211-220 reported results of clinical studies and confirmed that the WT1 vaccine was useful as cancer vaccine when administered by injection. The mucosal administration of the vaccine composition of the present invention could induce cellular immune response that is equivalent to or stronger than the immune response induced by injection in mice, and therefore, it is expected that the composition of the present invention can also effectively induce cellular immune response that is comparative to or stronger than that induced by injection. The composition of the invention is useful as a cancer vaccine.

What is claimed is:

1. A method for inducing cellular immunity in a subject, which comprises mucosally administering to the subject a cancer vaccine composition comprising:
   (i) a WT1 peptide and/or a modified WT1 peptide;
   (ii) a first cellular immunity induction promoter comprising a TLR7 ligand and a helper peptide.

2. The method according to claim 1, wherein the helper peptide is peptide-25.

3. The method according to claim 2, wherein the WT1 peptide is Db126 peptide.

4. The method according to claim 1, wherein the WT1 peptide is Db126 peptide.

5. The method according to claim 1, wherein mucosally administering comprises orally administering.

6. The method according to claim 1, wherein mucosally administering comprises sublingual administering.

7. The method according to claim 1, wherein mucosally administering comprises nasally administering.

8. The method according to claim 1, wherein the vaccine composition is in the form of a film preparation.

9. The method according to claim 1, wherein the vaccine composition is in the form of a liquid formulation.

10. The method according to claim 1, wherein the vaccine composition is in the form of an orally-disintegrating tablet.

11. The method according to claim 1, wherein the TLR7 ligand is TLR7-II or resiquimod.

12. The method according to claim 11, wherein the TLR7 ligand is TLR7-II.

13. The method according to claim 11, wherein the TLR7 ligand is resiquimod.

14. The method according to claim 11, wherein the helper peptide is peptide-25.

15. The method according to claim 14, wherein the WT1 peptide is Db126 peptide.

16. The method according to claim 11, wherein the WT1 peptide is Db126 peptide.

17. The method according to claim 11, wherein mucosally administering comprises orally administering.

18. The method according to claim 11, wherein mucosally administering comprises sublingual administering.

19. The method according to claim 11, wherein mucosally administering comprises nasally administering.

20. The method according to claim 11, wherein the vaccine composition is in the form of a film preparation.

21. The method according to claim 11, wherein the vaccine composition is in the form of a liquid formulation.

22. The method according to claim 11, wherein the vaccine composition is in the form of an orally-disintegrating tablet.

* * * * *

SEQUENCE LISTING

<160> NUMBER OF SEQ ID NOS: 10

<210> SEQ ID NO 1
<211> LENGTH: 9
<212> TYPE: PRT
<213> ORGANISM: Homo sapiens

<400> SEQUENCE: 1

Arg Met Phe Pro Asn Ala Pro Tyr Leu
1               5

<210> SEQ ID NO 2
<211> LENGTH: 9
<212> TYPE: PRT
<213> ORGANISM: Homo sapiens

<400> SEQUENCE: 2

Cys Met Thr Trp Asn Gln Met Asn Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Tyr Thr Trp Asn Gln Met Asn Leu
1               5

<210> SEQ ID NO 4
<211> LENGTH: 20
<212> TYPE: DNA
<213> ORGANISM: Unknown
<220> FEATURE:
<223> OTHER INFORMATION: Description of Unknown: Bacterial DNA
      sequence

<400> SEQUENCE: 4
tccatgacgt tcctgacgtt                                               20

<210> SEQ ID NO 5
<211> LENGTH: 15
<212> TYPE: PRT
<213> ORGANISM: Mycobacterium tuberculosis

<400> SEQUENCE: 5

Phe Gln Asp Ala Tyr Asn Ala Ala Gly Gly His Asn Ala Val Phe
1               5                   10                  15

<210> SEQ ID NO 6
<211> LENGTH: 18
<212> TYPE: PRT
<213> ORGANISM: Homo sapiens

<400> SEQUENCE: 6

Trp Ala Pro Val Leu Asp Phe Ala Pro Pro Gly Ala Ser Ala Tyr Gly
1               5                   10                  15

Ser Leu

<210> SEQ ID NO 7
<211> LENGTH: 13
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (3)..(3)
<223> OTHER INFORMATION: Cyclohexylalanine
<220> FEATURE:
<221> NAME/KEY: MOD_RES
<222> LOCATION: (13)..(13)
<223> OTHER INFORMATION: D-Ala

<400> SEQUENCE: 7

Ala Lys Ala Val Ala Ala Trp Thr Leu Lys Ala Ala Ala
1               5                   10

<210> SEQ ID NO 8
<211> LENGTH: 16
<212> TYPE: PRT
<213> ORGANISM: Homo sapiens

<400> SEQUENCE: 8

Lys Arg Tyr Phe Lys Leu Ser His Leu Gln Met His Ser Arg Lys His
1               5                   10                  15

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Lys Lys Lys Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Asp Pro Lys His Pro Lys Ser Phe
1               5
```